US006888627B2

(12) United States Patent
Leslie et al.

(10) Patent No.: US 6,888,627 B2
(45) Date of Patent: *May 3, 2005

(54) OPTICAL SCANNING SYSTEM FOR SURFACE INSPECTION

(75) Inventors: Brian C. Leslie, Cupertino, CA (US); Mehrdad Nikoonahad, Atherton, CA (US); Keith B. Wells, Santa Cruz, CA (US)

(73) Assignee: KLA-Tencor Corporation, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/411,646

(22) Filed: Apr. 10, 2003

(65) Prior Publication Data

US 2003/0206294 A1 Nov. 6, 2003

Related U.S. Application Data

(63) Continuation of application No. 09/571,303, filed on May 8, 2000, now abandoned, which is a continuation of application No. 08/868,292, filed on Jun. 3, 1997, now Pat. No. 6,081,325.
(60) Provisional application No. 60/018,973, filed on Jun. 4, 1996.

(51) Int. Cl.[7] ............................................. G01N 21/88
(52) U.S. Cl. .................................................. 356/237.2
(58) Field of Search ................. 356/237.1, 237.2–237.5

(56) References Cited

U.S. PATENT DOCUMENTS

| 3,851,951 | A | | 12/1974 | Eveleth |
| 4,230,940 | A | * | 10/1980 | Minami et al. .......... 250/201.4 |
| 4,240,442 | A | | 12/1980 | Andresen et al. |

(Continued)

FOREIGN PATENT DOCUMENTS

| EP | 065051 A2 | 12/1981 |
| EP | 0398781 | 11/1990 |
| JP | 62-128135 | 6/1987 |

(Continued)

OTHER PUBLICATIONS

"Accoustoopic Scanners and Modulators," Gottleib, M. Optical Scanning, ed. By G.F. Marshall, Dekker 1991, pp. 615–685.

"Dual Sensor Technology for High–Speed Detection of 0.1, Micron Defects." Alumot, D. et al., SPIE, vol. 1926, Integrated Circuit Metrology, Inspection and Process Control VII, 1193, pp. 1–12.

(Continued)

*Primary Examiner*—Richard A. Rosenberger
(74) *Attorney, Agent, or Firm*—Parsons Hsue & de Runtz LLP

(57) ABSTRACT

In an optical scanning system for detecting particles and pattern defects on a sample surface, a light beam is focused to an illuminated spot on the surface and the spot is scanned across the surface along a scan line. A detector is positioned adjacent to the surface to collect scattered light from the spot where the detector includes a one- or two-dimensional array of sensors. Light scattered from the illuminated spot at each of a plurality of positions along the scan line is focused onto a corresponding sensor in the array. A plurality of detectors symmetrically placed with respect to the illuminating beam detect laterally and forward scattered light from the spot. The spot is scanned over arrays of scan line segments shorter than the dimensions of the surface. A bright field channel enables the adjustment of the height of the sample surface to correct for errors caused by height variations of the surface. Different defect maps provided by the output of the detectors can be compared to identify and classify the defects. The imaging function of the array of sensors combines the advantages of a scanning system and an imaging system while improving signal/background ratio of the system.

163 Claims, 8 Drawing Sheets

U.S. PATENT DOCUMENTS

| | | |
|---|---|---|
| 4,277,178 A | 7/1981 | Cushing et al. |
| 4,306,808 A | 12/1981 | Vander Neut |
| 4,376,583 A | 3/1983 | Alford et al. |
| 4,378,159 A | 3/1983 | Galbraith |
| 4,391,524 A | 7/1983 | Steigmeier et al. |
| 4,405,238 A | 9/1983 | Grobman et al. |
| 4,441,124 A | 4/1984 | Heebner et al. |
| 4,526,468 A | 7/1985 | Steigmeier et al. |
| 4,556,290 A | 12/1985 | Roulot |
| 4,589,773 A | 5/1986 | Ido et al. |
| 4,598,997 A | 7/1986 | Steigmeier et al. |
| 4,601,576 A | 7/1986 | Galbraith |
| 4,614,427 A | 9/1986 | Koizumi et al. |
| 4,650,983 A | 3/1987 | Suwa |
| 4,676,637 A | 6/1987 | Uto et al. |
| 4,728,190 A | 3/1988 | Knollenberg |
| 4,740,708 A | 4/1988 | Batchelder |
| 4,748,333 A | 5/1988 | Mizutani et al. |
| 4,752,898 A | 6/1988 | Koenig |
| 4,766,324 A | 8/1988 | Saadat et al. |
| 4,772,126 A | 9/1988 | Allemand et al. |
| 4,786,815 A | 11/1988 | Walker et al. |
| 4,794,264 A | 12/1988 | Quackenbos et al. |
| 4,800,268 A | 1/1989 | Miyoshi et al. |
| 4,844,617 A | 7/1989 | Kelderman et al. |
| 4,864,123 A | 9/1989 | Mizutani et al. |
| 4,864,147 A | 9/1989 | Ikari et al. |
| 4,889,998 A * | 12/1989 | Hayano et al. .......... 356/239.8 |
| 4,895,446 A | 1/1990 | Maldari et al. |
| 4,898,471 A | 2/1990 | Stonestrom et al. |
| 4,899,055 A | 2/1990 | Adams |
| 4,912,487 A | 3/1990 | Porter et al. |
| 4,936,676 A | 6/1990 | Stauffer |
| 4,966,455 A | 10/1990 | Avni et al. |
| 4,966,457 A | 10/1990 | Hayano et al. |
| 4,998,019 A | 3/1991 | Stokowski et al. |
| 4,999,510 A | 3/1991 | Hayano et al. |
| 5,004,929 A | 4/1991 | Kakinoki et al. |
| 5,027,132 A | 6/1991 | Manns et al. |
| 5,076,692 A | 12/1991 | Neukermans et al. |
| 5,083,035 A | 1/1992 | Pecen et al. |
| 5,092,557 A | 3/1992 | Sawatzki |
| 5,122,898 A | 6/1992 | Picault |
| 5,125,741 A * | 6/1992 | Okada et al. ............ 356/237.2 |
| RE33,991 E | 7/1992 | Shiba et al. |
| 5,133,635 A | 7/1992 | Malin et al. |
| 5,162,642 A | 11/1992 | Akamatsu et al. |
| 5,166,516 A | 11/1992 | Kajimura |
| 5,168,386 A | 12/1992 | Galbraith |
| 5,189,481 A | 2/1993 | Jann et al. |
| 5,241,366 A | 8/1993 | Bevis et al. |
| 5,264,912 A | 11/1993 | Vaught et al. |
| 5,272,517 A | 12/1993 | Tokura |
| 5,274,434 A | 12/1993 | Morioka et al. |
| 5,317,380 A | 5/1994 | Allemand |
| 5,363,187 A | 11/1994 | Hagiwara et al. |
| 5,436,464 A | 7/1995 | Hayano et al. |
| 5,461,474 A | 10/1995 | Yoshii et al. |
| 5,479,252 A | 12/1995 | Worster et al. |
| 5,530,550 A | 6/1996 | Nikoonahad et al. |
| 5,576,831 A | 11/1996 | Nikoonahad et al. |
| 5,633,747 A | 5/1997 | Nikoonahad et al. |
| 5,659,390 A | 8/1997 | Danko |
| 5,667,353 A | 9/1997 | Drake |
| 5,699,447 A | 12/1997 | Alumot et al. |
| 5,712,701 A | 1/1998 | Clementi et al. |
| 5,742,422 A | 4/1998 | Drake |
| 5,767,962 A * | 6/1998 | Suzuki et al. ............ 356/237.2 |
| 5,805,278 A | 9/1998 | Danko |
| 5,883,710 A | 3/1999 | Nikoonahad et al. |
| 5,888,710 A | 3/1999 | Adachi et al. |
| 5,903,342 A | 5/1999 | Yatsugake et al. |
| 6,081,325 A | 6/2000 | Leslie et al. |
| 6,118,525 A | 9/2000 | Fossey et al. |
| 6,215,551 B1 | 4/2001 | Nikoonahad et al. |
| 6,292,259 B1 | 9/2001 | Fossey et al. |

FOREIGN PATENT DOCUMENTS

| | | |
|---|---|---|
| JP | 62-153737 | 7/1987 |
| JP | 62-274633 | 11/1987 |
| JP | 63-73635 | 4/1988 |
| JP | 63-284455 | 11/1988 |
| JP | 2-78936 | 3/1990 |
| JP | 2-87047 | 3/1990 |
| JP | 3-225939 | 10/1991 |
| JP | 5-332946 | 12/1993 |
| JP | 6-34559 | 2/1994 |
| JP | 62-174655 | 6/1994 |
| WO | 96-18093 | 6/1996 |

OTHER PUBLICATIONS

"New Laser Scanning Techniques for Wafer Inspection," M. Nikoonahad, SPIE, vol. 2638, Feb. 1995, pp. 285–301.

"Inspection of Patterned Wafers: 0.35 μm Design Rules and Beyond," J. R. Dralla, presented at Semicon Kansai, Jun. 15–17, 1994, pp. 1–8.

"Dynamic Performance of a Scanning X–Y Stage for Automated Electron–beam Inspection," D. J. Clark et al., J. Vac. Sci. Technol. B. vol. 10, No. 6, Nov./Dec. 1992, pp. 2638–2642.

"A Stand–Alone Scanning Force and Friction Microscope," M. Hipp et al. Ultramicroscopy, 42–44, 1992, pp. 1498–1503**.

"Experimental Scattering Investigations and Radiative Transfer Calculations of Large Arbitrarily Shaped Absorbing Particles," C. Sasse, SPIE Optical Scattering, vol. 1995, 1993, pp. 294–299**.

"Meeting the Challenges of Unpatterned Wafer Inspection for 130nm Device Geometries," H. Altendorfer et al., Silicon Wafer Symposium, SEMI 1998, pp. K–1–K–8**.

"COPs/Particles Discrimination with a Surface Scanning Inspection System," M. Akbulut et al., Semiconductor International, Apr. 1999, pp. 1–6**.

"Comparison of Models and Measurements of Scatter from Surface Bound Particles," C.A. Scheer et al. SPIE, vol. 3275, pp. 102–111**.

"Comparison of Measured and Modeled Scatter from Defects and Particles on Silicon Wafers," J.C. Stover et al., Electromagnetic and Light Scattering: Theory and Applications, Workshop 1997, pp. 109–118**.

"Experimental Verification of Discrete Sources Method in Problem of Light Scattering From Particle Upon Wafer Surface," pp. 1–6 with 6 sheets of figures**.

"Response of a Wafer Surface Scanner to Non–Ideal, Real World Particles," S. Chae et al., Particle Technology Laboratory Publication No. 820, Jan. 1992, 10 pages**.

"Using Calibration Curve Modeling for Scanning Surface Inspection Systems," R.S. Howland et al., Analytical Technologies, Jul./Aug. 1995 MICRO, pp. 61–71**.

"Measurement of Hemispherical Directional Reflectance in the Infared." J.T. Neu, SPIE, Optical Scanning vol. 1995, 1993**.

"Discrete Sources Method For The Silicon Wafers Defect Discrimination," Yuri Eremin and N. Orlov, J. $12^{th}$ Annual Review of Progress in Applied Computational Electromagnetics, Mar. 18–22, 1996, pp. 758–763**.

"Determination of COP Distribution After SCI Cleaning By A Laser Particle Counter," T. Fujise et al., Optical Characterization Techniques for High–Performance Microelectronic Device Manufacturing III, SPIE Proc. vol. 2877, Oct. 16, 1998, pp. 16–25**.

"Acoustooptic Devices and Applications," Chang, IEEE Transactions on Sonics and Ultrasonics, vol. Su–23, No. 1, Jan. 1976, pp. 1–22**.

"Optical Considerations for an Acoustooptic Deflector," Dickson, Applied Optics, vol. II, No. 10, Oct. 1972, pp. 2196–2202**.

"Design Considerations for Acousto–optic Devices," Young Jr. et al., Proceedings of IEEE, vol. 69, Jan. 1981, pp. 54–64**.

"Acoustooptic Deflection Materials and Techniques," Uchida et al., Proceedings for the IEEE, vol. 61, No. 8, Aug. 1973, pp. 1073–1092**.

"Modulation Transfer Characteristics of an Acoustooptic Deflector," Randolph et al., Applied Optics, vol. 10, No. 6, Jun. 1971, pp. 1383–1385**.

"High Speed Laser Facsimile Scanner," Grossman et al., SPIE, Laser Recording and Information Handling, vol. 200, 1979, pp. 8–15**.

"High Resolution Acoustooptic Deflector Demonstrated in a Laser Scanner," Merry, pp. 32–34**.

"All About Bragg Angle Errors in Acousto–optic Modulators and Deflectors," ISOMET, May 1993, pp. 1–23**.

"Acousto–optical Deflectors," Bademian, ISOMET, May 1993, pp. 1–32**.

"Acousto–optical Deflectors," ISOMET, pp. 1–9**.

ISOMET Corporation Specification for LS–55 V Acousto Optic Deflector/AOT, 4 pages**.

Fossey, Michael E., "System Architecture and Design Next Generation Wafer Inspection System", Jul. 25, 1994, ADE Optical Systems**.

Fossey, Michael E.; Hunt, Jim; Clementi, Lee, "Engineering Requirements Document, Galaxy, Advanced Wafer Inspection Station", Draft Revision 0.1, Jun. 13, 1995, ADE Optical Systems**.

Fossey, Michael E., "Calibration, Signal & Data Processing for Galaxy AWIS Beta Units", Sep. 26, 1996, ADE Optical Systems**.

"A WIS, 300mm Advanced Wafer Inspection System", Apr. 6, 1996, ADE Optical Systems**.

Particle Scattering Project (PSP), Work Product of SABIT Interns (3), Sep. 27, 1995, ADE Optical Systems**.

European Search Report—mailed Jun. 25, 1999.

"Imaging Systems: Detectors of the Past, Present, and Future," S. McGeorge, Spectroscopy, Vo. 2, No. 4, 1987.

"Diffuse Reflection From Smooth Dielectric Surfaces," L. Wolff, SPIE Optical Scattering, vol. 1995, 1993, pp. 26–44.

"Plane–wave Expansions Methods Applied ot the Calculation of the Optical Scattering by One–dimensional Randomly Rough Dielectric Surfaces," S, Mainguy, SPIE Optical Scattering, vol. 1995, 1993, pp. 45–56.

"The Wavelength Dependence of Scatter From O–50 Grade Beryllium Mirrors," C.M. Egert et al., SPIE Optical Scattering, vol. 1995, 1993, pp. 57–65.

"Extracting the Scattering Coefficient of Sea Water From the Return Time Signal of Ocean Lidar," J. Zhang et al., SPIE Optical Scattering, vol. 1995, 1993, pp. 74–78.

"Preparing Samples for Scattering Measurements—A Cleaning Study: Part 2," J. Brown, SPIE Optical Scattering, vol. 1995, 1993, pp. 80–91.

"Design Review of an Instrument to Map Low Level Hydrocarbon Contamination," B. D. Swimley et al. SPIE Optical Scattering, vol. 1995, 1993, pp. 92–100.

"Measurement of Hemispherical Directional Reflectance in the Infrared," J. T. Neu, SPIE Optical Scattering, vol. 1995, 1993, pp. 101–120.

"Design Review of a High Accuracy UV to Near IR Scatterometer," T. F. Schiff et al., SPIE Optical Scattering, vol. 1995, 1993, pp. 121–130.

"Design Review of Unique Laser Monostatic Bidirectional Reflectometer," Z. Gu et al., SPIE Optical Scattering, vol. 1995, 1993, pp. 131–142.

"Sources of Error in Spectroscopic, Low Level Integrated Light Scattering Measurements," D. Rönnow, SPIE Optical Scattering, vol. 1995, 1993, pp. 143–151.

"A New Generation High Speed, High Resolution, Hemispherical Scatterometer," R. J. Catonguay, SPIE Optical Scattering, vol. 1995, 1993, pp. 152–165.

"Real–time Detection of Surface Damage by Direct Assessment of the BRDF" H. Rothe et al. SPIE Optical Scattering, vol. 1995, 1993, pp. 168–180.

"Microtopography Investigations of Optical Surfaces and Thin Films by Light Scattering, Optical Profilomety, and Atomic Force Microscopy," A. Duparré et al., SPIE Optical Scattering, vol. 1995, 1993, pp. 181–192.

"Characterization of Curved Plastic Surfaces," Q.Y. Xie et al. SPIE Optical Scattering, vol. 1995, 1993, pp. 193–201.

"Reflection, Scattering, and Polarizaton From a Very Rough Black Surface," S.F. Nee et al., SPIE Optical Scattering, vol. 1995, 1993, pp. 202–212.

"Very High Angular Selectivity System for Measuring Backscatter from Rough Surfaces." Y. Takakura et al. SPIE Optical Scattering, vol. 1995, 1993, pp. 213–222.

"Scattering Properties of Very Rough Surfaces: Applications to Brightness Measurement of Common Objects," P. Sandoz et al., SPIE Optical Scattering, vol. 1995, 1993, pp. 223–234.

"A Step–Height Standard for Surface Profiler Calibration," P. Z. Takacs et al. SPIE Optical Scattering, vol. 1995, 1993, pp. 235–244.

"High Temperature Optical Scatter Characteristics of CVD Diamond and Natural Type IIa Diamond," M.B. McIntosh et al., SPIE Optical Scattering, vol. 1995, 1993, pp. 264–255.

"Wavelength Scaling Investigation of Several Materials," J.C. Stover et al. SPIE Optical Scattering, vol. 1995, 1993, pp. 256–266.

"Mueller Matrix Measurements of Several Optical Components," J.C. Stover et al. SPIE Optical Scattering, vol. 1995, 1993, pp. 267–272.

"Bulk Scatter Measurements in Fused Silica at Two Wavelengths: A Comparison with Rayleigh Scatter Theory," J.P. Black et al., SPIE Optical Scattering, vol. 1995, 1993, pp. 273–284.

"BRDF Round Robin Test of ASTME E1392," T.A. Leonard et al., SPIE Optical Scattering, vol. 1995, 1993, pp. 285–293.

"Scatterometers Improve Laser Mirrors," G. Valliant, TMA Technologies, Inc. Photonics Spectra, vol. 25, Issue 8, Aug. 1991, p. 100.

"Windowing Effects on Light Scattering by Sinusoidal Surfaces," E. Marx et al., SPIE Optical Scattering, vol. 1995, 1993, pp. 2–14.

"A Light Scattering and Distribution Model for Scintillation Cameras," S. Rioux et al., SPIE Optical Scattering, vol. 1995, 1993, pp. 15–25.

\* cited by examiner

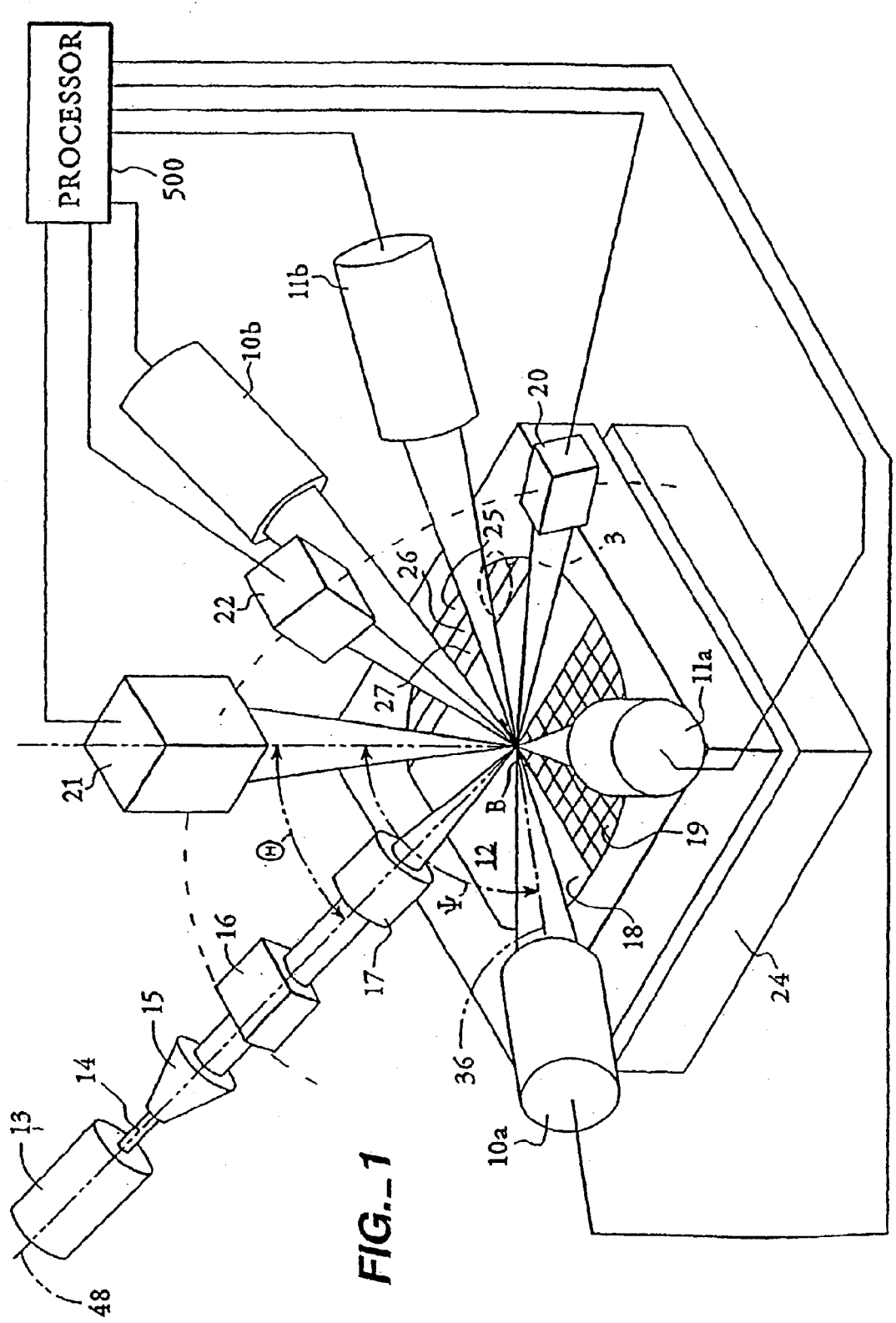
FIG._1

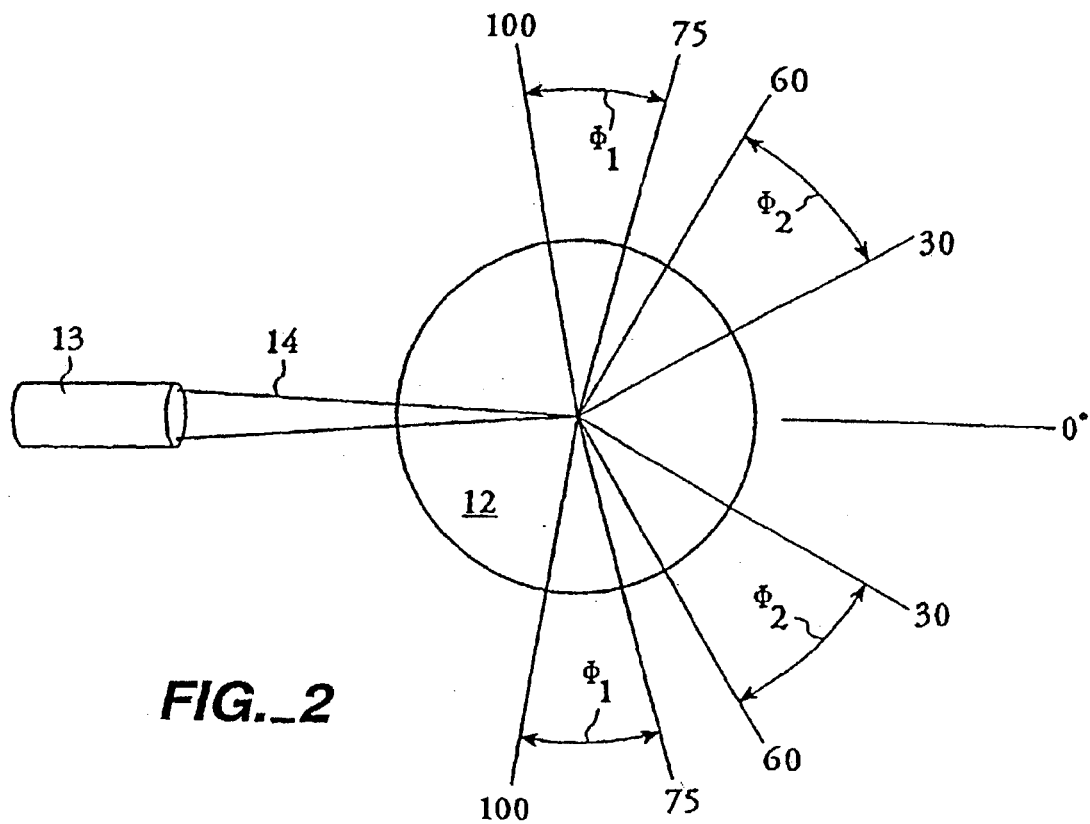
FIG._2
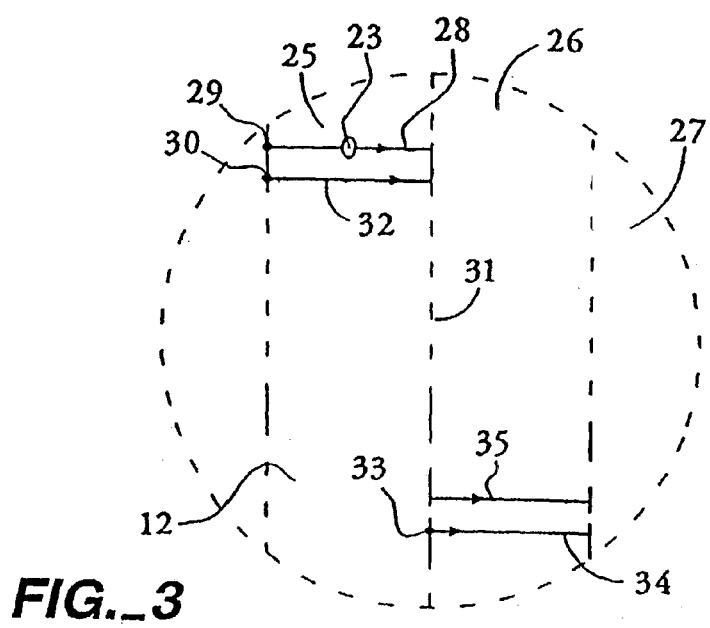
FIG._3

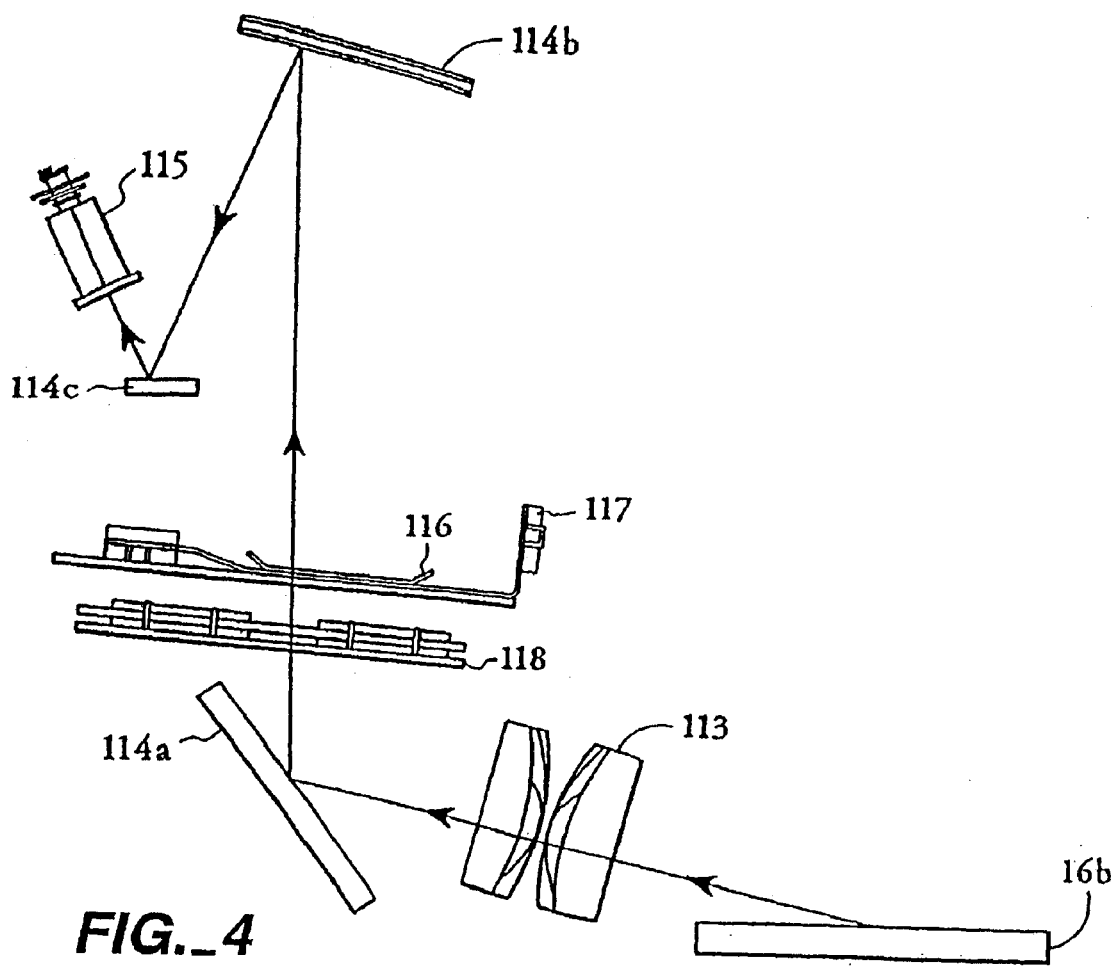
FIG._4
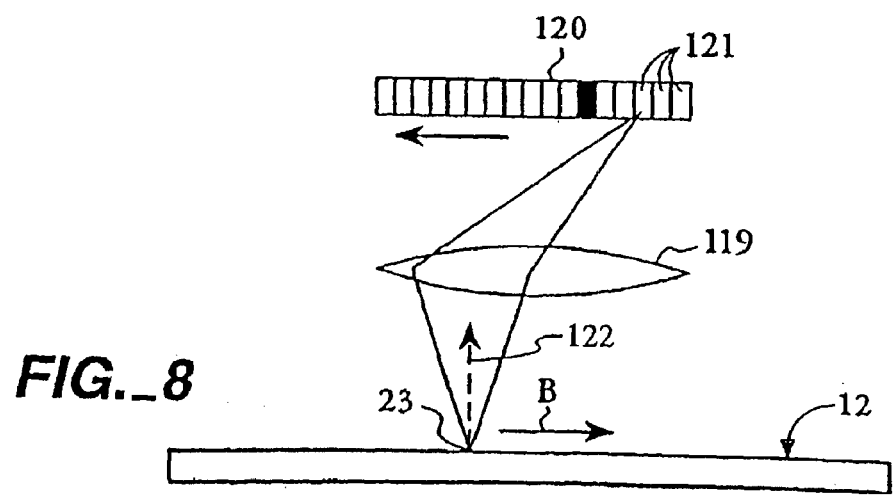
FIG._8

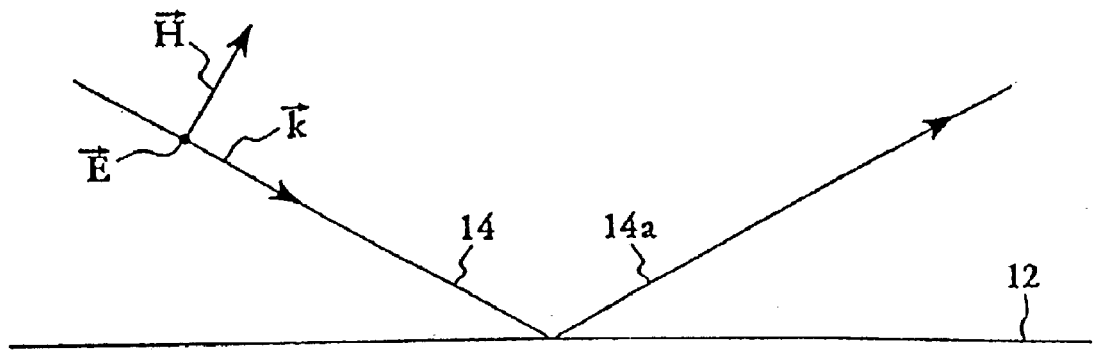
FIG._5A
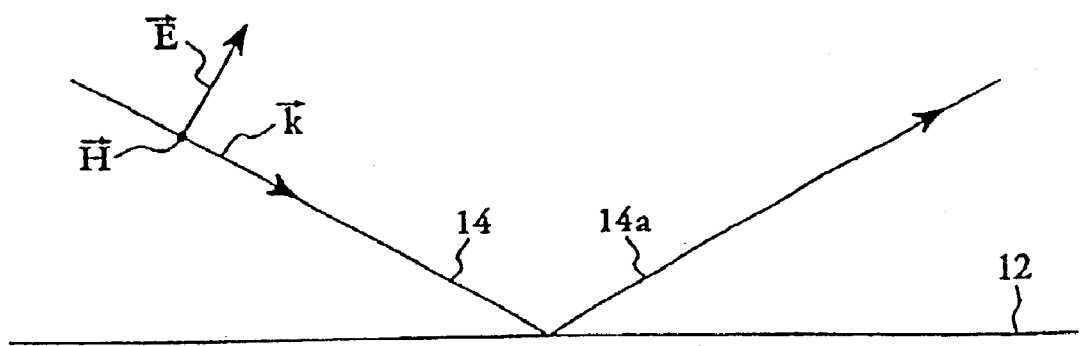
FIG._5B

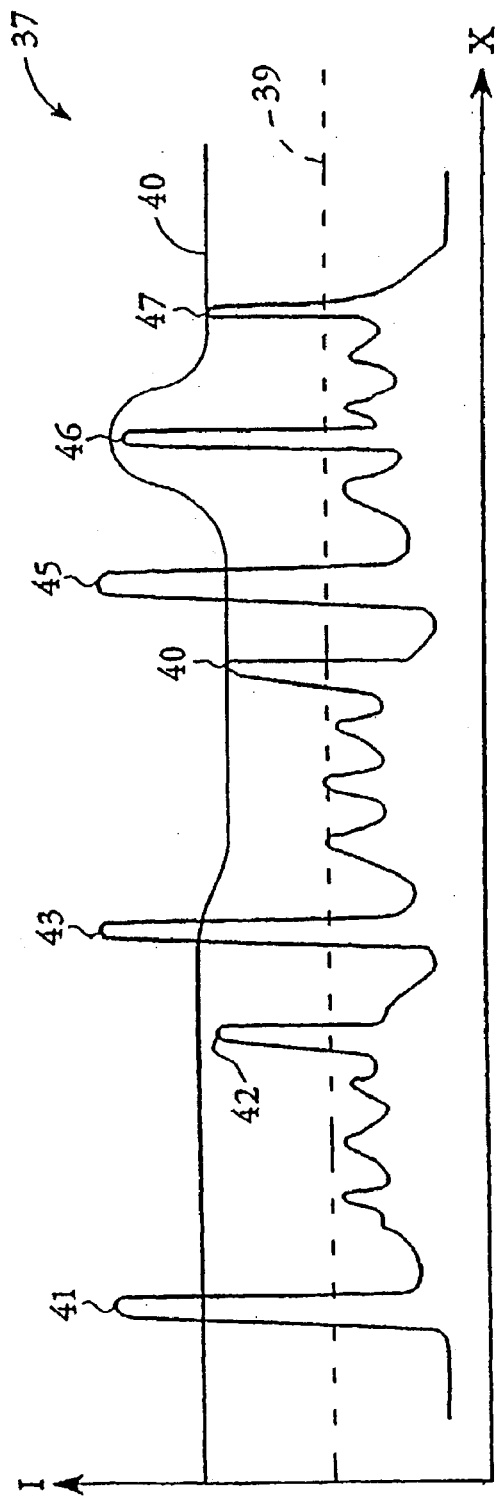
FIG._6
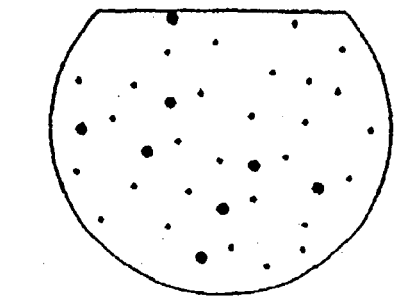
FIG._7E
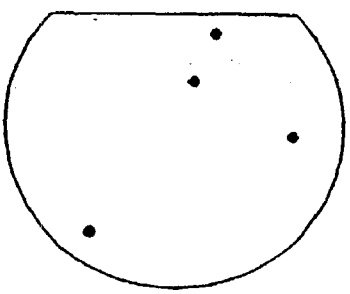
FIG._7D
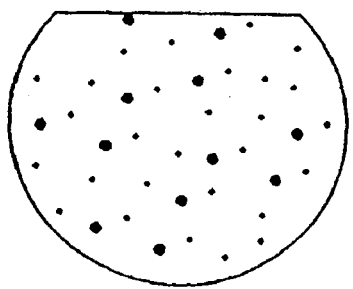
FIG._7C
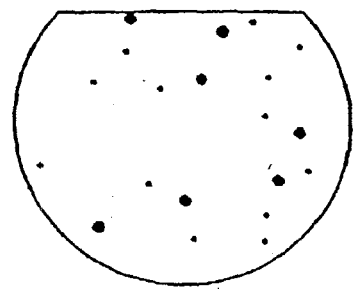
FIG._7B
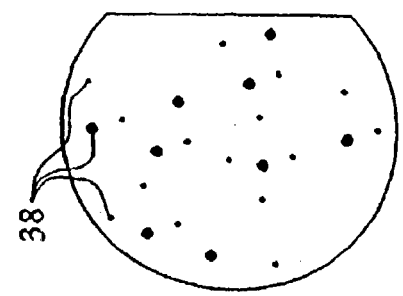
FIG._7A

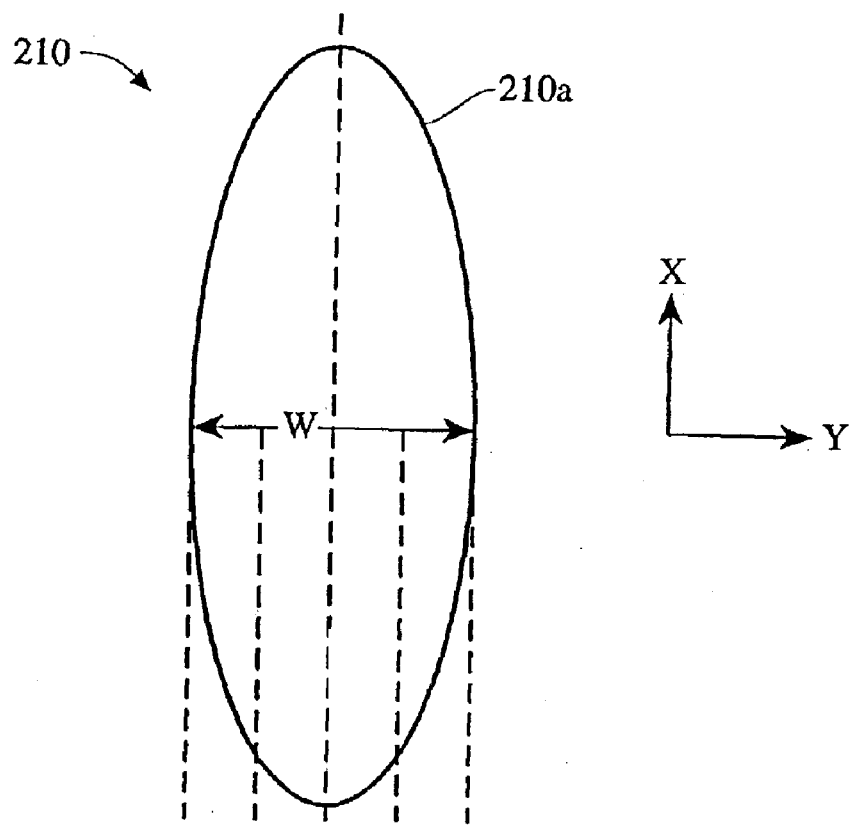
FIG._9A
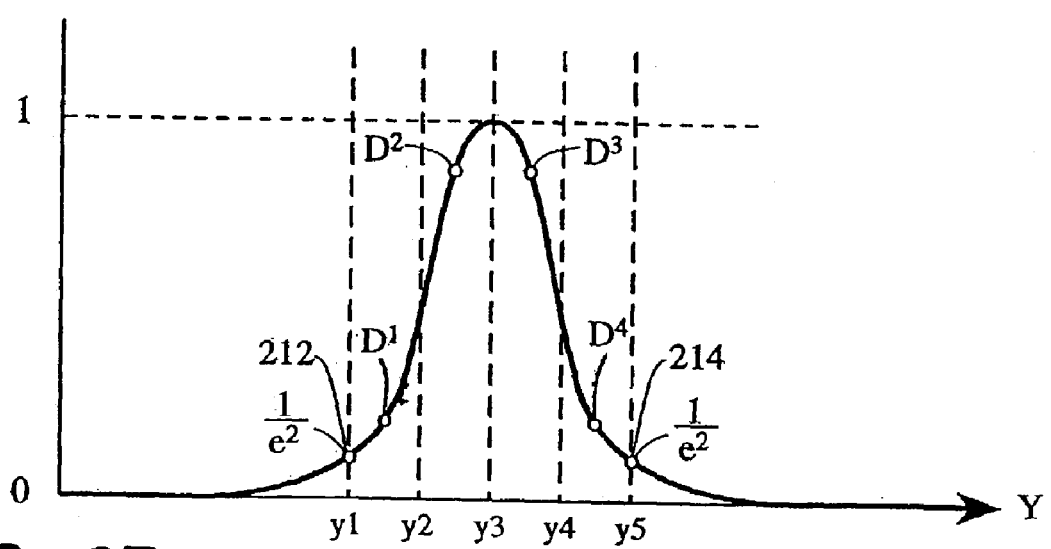
FIG._9B

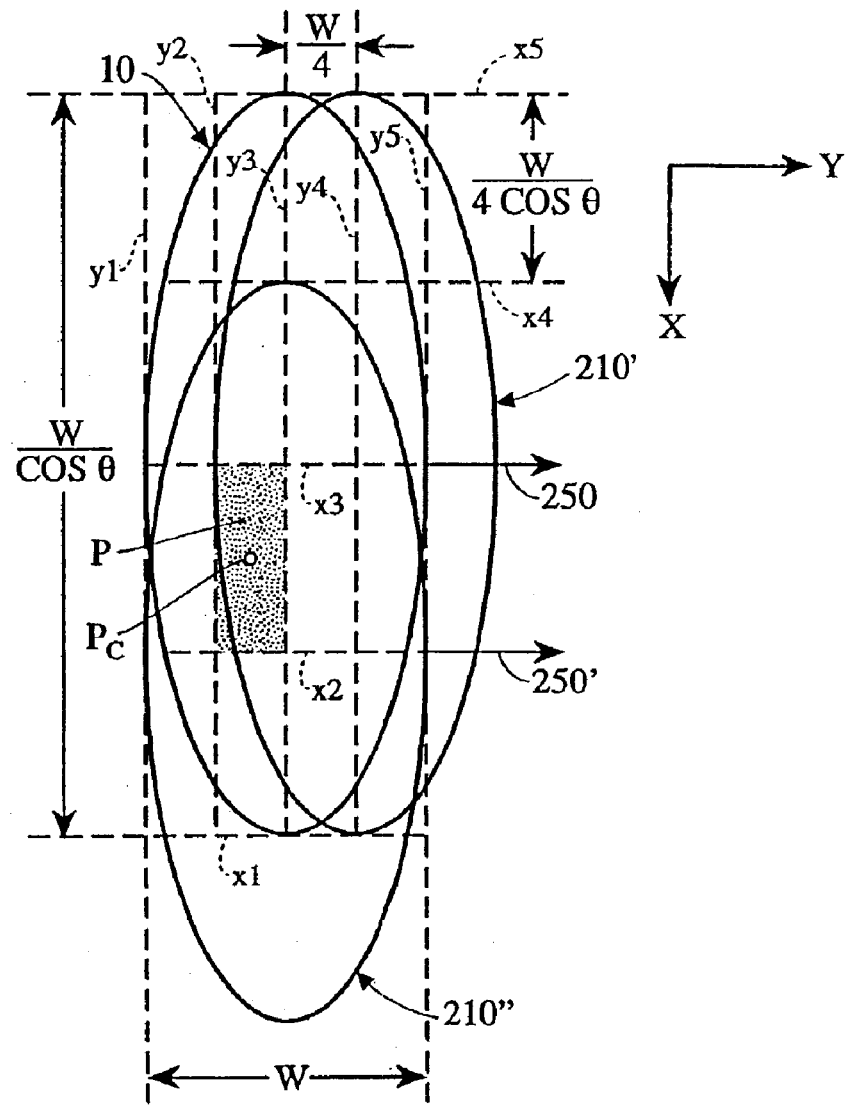
FIG._9C
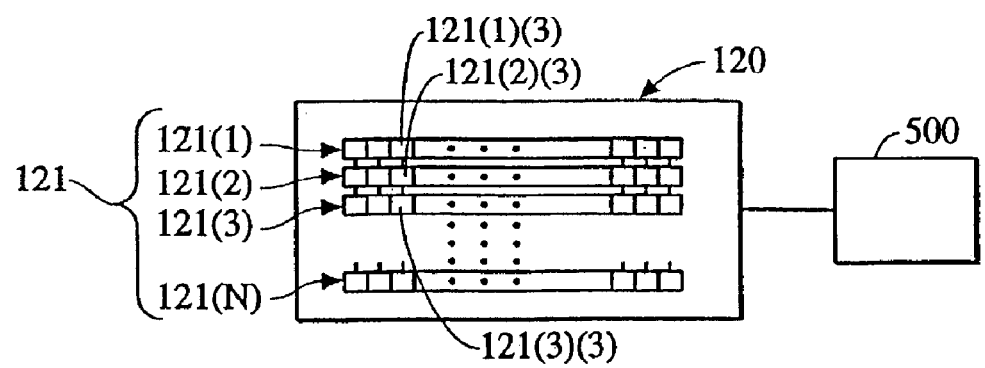
FIG._11

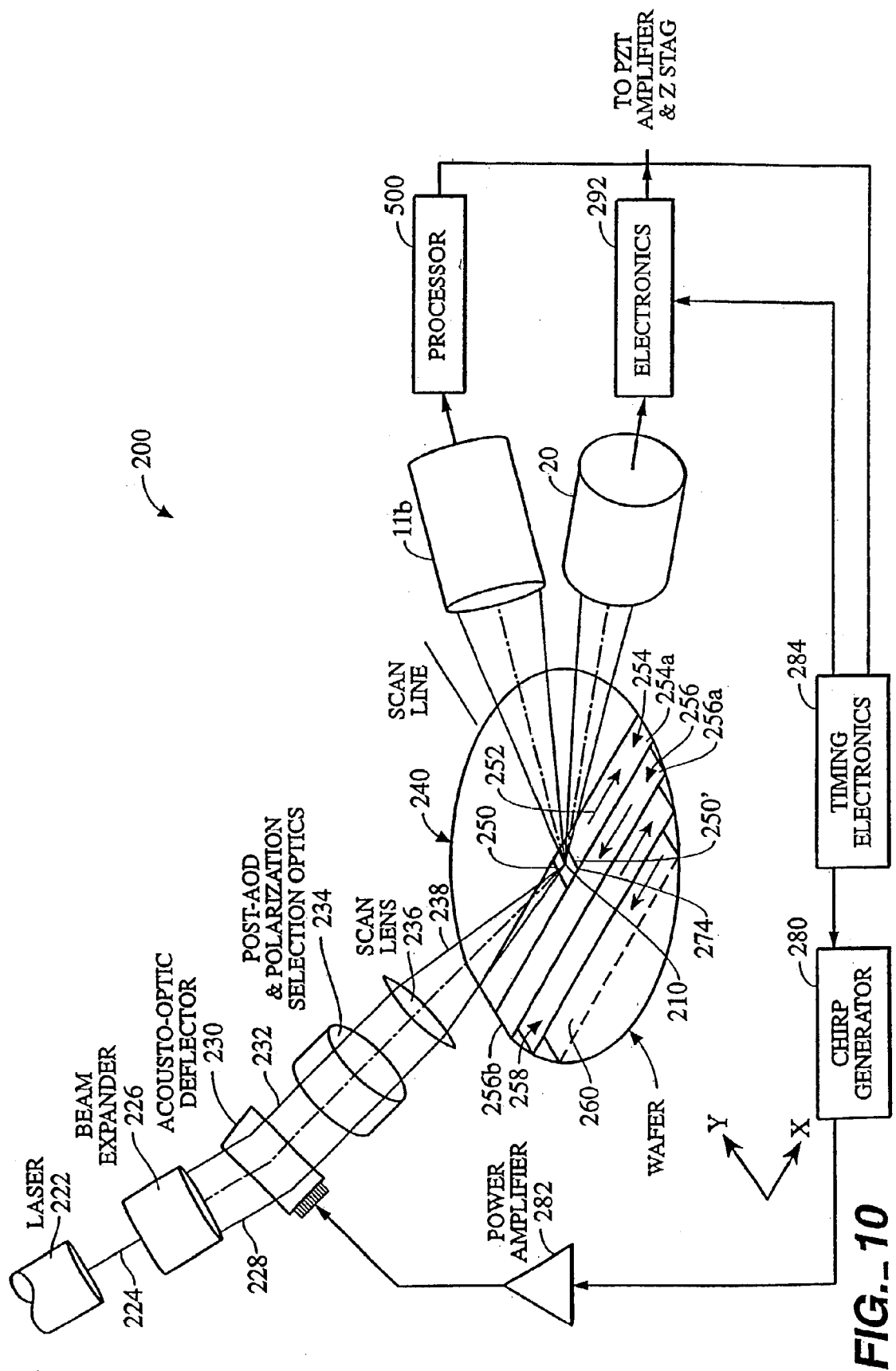
FIG._10

OPTICAL SCANNING SYSTEM FOR SURFACE INSPECTION

This application is a continuation of U.S. patent application Ser. No. 09/571,303, filed May 8, 2000, now abandoned, which is a continuation of U.S. patent application Ser. No. 08/868,292, filed Jun. 3, 1997, now U.S. Pat. No. 6,081,325, which claims benefit of Ser. No. 60/018,973, filed Jun. 4, 1996.

BACKGROUND OF THE INVENTION

The present invention pertains to the field of optical surface inspection. Specifically, the present invention pertains to illumination and light collection optics for inspecting semiconductor wafers and the like.

Monitoring anomalies, such as pattern defects and particulate contamination, during the manufacture of semiconductor wafers is an important factor in increasing production yields. Numerous types of defects and contamination, especially particles, can occur on a wafer's surface. Determining the presence, location and type of an anomaly on the wafer surface can aid in both locating process steps at which the anomaly occurred and determining whether a wafer should be discarded.

Originally, anomalies were monitored manually by visual inspection of wafer surfaces for the presence of particulate matter. These anomalies, usually dust or microscopic silicon particles, caused many of the wafer pattern defects. However, manual inspection proved time-consuming and unreliable due to operator errors or an operator's inability to observe certain defects. The ever increasing size of the wafer surface, along with the decreasing dimensions of the components thereon, resulted in a sharp increase in the number of components on the wafer's surface. The need for automation became manifest.

To decrease the time required to inspect wafer surfaces, many automatic inspection systems were introduced. A substantial majority of these automatic inspection systems detect anomalies based on the scattering of light. For example, see U.S. Pat. No. 4,601,576 to L. Galbraith, assigned to the assignee of the present invention. These systems include two major components: illumination optics and collection-detection optics. Illumination optics generally consists of scanning a wafer surface with a coherent source of light, e.g., a laser. Anomalies present on the wafer's surface scatter incident light. The collection optics detect the scattered light with reference to the known beam position. The scattered light is then converted to electrical signals which can be measured, counted and displayed as bright spots on an oscilloscope or other monitor.

The illumination optics plays a major role in establishing the detection sensitivity of the inspection system. The sensitivity is dependent upon the size of the spot scanned on the wafer and the illumination angle. The smaller the spot size, the more sensitive the system is to detecting anomalies. However, decreasing the spot size increases the time required to scan the wafer surface and therefore reduces throughput.

The sensitivity of both the illumination and collection-detection optics is dependent upon the texture of the surface of the wafer illuminated. If the surface illuminated is patterned, this reduces the sensitivity of the system because such areas produce scatter which makes it difficult to determine the presence of an anomaly. To abrogate scatter due to patterned features, the angle of incidence of the spot on the surface is increased, with respect to the normal to the surface. However, too great of an angle, i.e., a grazing angle with respect to the surface, will also reduce the sensitivity of the system. Moreover, increasing the angle of incidence, increases the effective size of the spot, thereby reducing the sensitivity of the system. Thus, a trade-off exists between sensitivity and inspection rate of the system. The sensitivity of the collection-detection optics is generally a factor of the detector's azimuthal position with respect to the scanning beam and elevation.

Accordingly, many illumination and collection-detection techniques have been proposed that take advantage of the aforementioned concepts. In addition, efforts have been made to provide for constant scanning of the wafer's surface to further increase the speed of the inspection. In U.S. Pat. No. 5,317,380, Allemand discloses a beam of laser light brought to focus as an arcuate scan line on a surface, at a grazing angle of incidence. A pair of light detectors are provided to collect light which is scattered away from the beam in a forward direction so that the angle of collection is constant over the entire scan line.

U.S. Pat. No. 4,912,487 to Porter et al. discloses a laser pattern writing and inspection system that illuminates a target surface with an argon ion laser beam. An acousto-optical deflector is driven with a chirp signal and placed in the path of the beam to cause it to sweep out raster scan lines. The target is placed on a stage capable of bi-directional movement. The beam has an angle of incidence normal to the target and the stage moves so that it is scanned along adjacent contiguous strips of equal width.

U.S. Pat. No. 4,889,998 to Hayano et al., discloses an apparatus and method for detecting foreign particles on a pellicle using a beam of light that is scanned across the pellicle with light detected by a plurality of detectors grouped in pairs. Two pairs of detectors are positioned to collect rearwardly scattered light. The difference in intensity of scattered light detected by each detector is monitored, whereby the position of the particle on the pellicle is determined by analyzing the intensity variations.

In U.S. Pat. No. 4,898,471 to Stonestrom et al., an apparatus and method for detecting particles on a patterned surface is disclosed wherein a single light beam is scanned, at a grazing angle of incidence, across the surface. The surface contains a plurality of identical dies with streets between them. With the beam scanning parallel to the streets, a single channel collection system detects scattered light from an azimuthal angle that maximizes particle signals while reducing pattern signals. A processor constructs templates from the detected light which corresponds to individual dies and then compares the templates to identify particles on the dies.

In U.S. Pat. No. 4,617,427, Koizumi et al., a wafer is mounted on a feed stage connected to a rotary drive which provides a constant speed helical scan of a wafer surface. An S-polarized laser beam is scanned thereon at varying angles of incidence. The angle of incidence is dependent upon whether the wafer is smooth or patterned. A single detector is positioned perpendicular to the wafer's surface for collecting scattered light and includes a variable polarization filter that attenuates scattered light in an S polarization state, when the surface is patterned, and does not attenuate light if the wafer is smooth.

In U.S. Pat. No. 4,441,124 to Heebner, a laser is scanned over the surface of a wafer at an angle normal thereto. The laser beam is scanned by deflecting it with a galvanometer and an acousto-optic deflector in synchronization with the scanning beam rate of a video monitor. A photodetector employing a ring-type collection lens monitors the intensity of light scattered substantially along the wafer surface. This arrangement was employed to take advantage of the finding that a patterned wafer having no particulate matter thereon will scatter substantially no light along the wafer surface, while a wafer having particulate matter on it will scatter a portion of the light impinging thereon along the surface.

Another particle detection apparatus and method is disclosed in U.S. Pat. No. 4,391,524, to Steigmeier et al., wherein a laser beam is scanned at an angle normal to the wafer's surface. In addition to rotating, the wafer stage is provided with movement along one axis that results in the wafer being scanned in a spiral fashion. A single detector is positioned perpendicular to the surface to collect scattered light. Threshold circuitry is employed to discriminate between the defects monitored.

It is an object of the present invention to provide a high-speed apparatus which is capable of scanning a laser beam across the surface of either a patterned or unpatterned wafer to detect anomalies thereon with sizes on the order of a fraction of a micron.

It is a further object of the present invention to classify detected anomalies and determine their size while increasing the confidence and accuracy of the detection system by reducing false counts.

SUMMARY OF THE INVENTION

These objects have been achieved with an apparatus and method for detecting anomalies of sub-micron size, including pattern defects and particulate contaminants, on both patterned and unpatterned wafer surfaces. For the purposes of this application, a particulate contaminant is defined as foreign material resting on a surface, generally protruding out of the plane of the surface. A pattern defect may be in or below the plane of the surface and is usually induced by contaminants during a photolithographic processing step or caused by crystal defects in the surface.

One aspect of the invention is directed towards an optical scanning system for detection of anomalies, such as particles and pattern defects on a surface, comprising means for directing a focused beam of light onto a sample surface to produce an illuminated spot thereon and means for scanning the spot across the surface along a first scan line. The system further comprises a first detector positioned adjacent to said surface to collect scattered light from the spot wherein the detector includes a one-dimensional or two-dimensional array of sensors and means for focusing scattered light from the illuminated spot at each of a plurality of positions along the scan line onto a corresponding sensor in the array.

Another aspect of the invention is directed towards an optical scanning method for detection of anomalies, such as particles and patterns on a surface, comprising the steps of directing a focused beam of light onto a sample surface to produce an illuminated spot thereon; scanning a spot across the surface along a first scan line; positioning a first detector adjacent to said surface to collect scattered light from the spot, wherein the detector includes a one-dimensional or two-dimensional array of sensors; and focusing scattered light from the illuminated spot at each position along the scan line onto a corresponding sensor in the array.

BRIEF DESCRIPTION OF THE DRAWINGS

FIG. 1 is a simplified perspective plan view of the illumination and collection optics of the present invention.

FIG. 2 is a top view of the illumination and collection optics shown in FIG. 1.

FIG. 3 is a detailed view showing the scan path of a spot on a wafer surface.

FIG. 4 is a detailed view of a collection channel shown in FIG. 1.

FIGS. 5A–5B is a plan view showing a polarization scheme employed by the present invention.

FIG. 6 is a graph of an electrical signal amplitude (I) versus beam scan position (X) on a wafer produced by the method of the present invention using the apparatus shown in FIG. 1.

FIGS. 7A–7E is a top view of a display derived from a scan of the wafer, as shown in FIG. 3.

FIG. 8 is a plan view of an imaging channel shown in FIG. 1.

FIG. 9A is a schematic view of an elliptical-shaped illuminated area or spot on a surface to be inspected to illustrate the invention.

FIG. 9B is a graphical illustration of the illumination intensity across the width or short axis of the elliptical spot of FIG. 9A for defining a boundary of the spot and to illustrate a point spread function of the illumination beam.

FIG. 9C is a schematic view of three positions of an illuminated spot on a surface to be inspected to illustrate the scanning and data gathering process of the system of this invention.

FIG. 10 shows partially in perspective and partially in block diagram form a system for inspecting anomalies of a semiconductor wafer surface to illustrate the preferred embodiment of the invention.

FIG. 11 is a block diagram of the imaging channel two-dimensional array detector of FIG. 8 and of a processor for controlling the detector and for synchronizing the transfer of signals in the detector with the scanning of light beam in FIGS. 1 and 10.

For simplicity in description, identical components are identified by the same numerals in this application.

DETAILED DESCRIPTION OF THE PREFERRED EMBODIMENTS

The present invention, as shown in FIG. 1 is based on the discovery that the scattering cross section of an anomaly on a patterned surface is asymmetrical. This in part is due to the asymmetry of the anomaly itself, or, in the case of particulate contaminants, the pattern on which a particulate rests changing the effective scattering cross section of the particle. Taking advantage of this discovery, a plurality of detectors are provided that includes groups of collector channels symmetrically disposed about the circumference of the surface. Although a greater number of collector channels may be employed in each group, the preferred embodiment uses two groups of two collector channels, 10a–b and 11a–b, disposed symmetrically about the wafer surface 12 so that each collector channel within a pair is located at the same azimuthal angle on opposite sides of the scan line, indicated by the line B. With collector channels positioned symmetrically in the azimuth, a substantial reduction in false counts can be obtained. For example, an anomaly having a symmetrical scattering cross section, will cause scattered light to impinge on a pair of collector channels, disposed symmetrically in the azimuth, with the same intensity. Anomalies with an asymmetrical scattering cross section will impinge on the same pair of collector channels with varying intensities. By comparing data representing the intensity of light impinging on symmetrically disposed collector channels, signals which are in common, such a pattern signals, may be discarded.

This provides a high confidence level that the resulting signals are in fact anomalies, and not due to random scattering by surface features. The data from the channels is compared by performing various algorithms and logical operations, e.g., OR, AND and XOR. In addition, examining the data concerning the anomalies having unidentical signals in the two channels allows determining the shape and/or composition of them.

As shown in FIG. 1, a light source 13, typically a laser, emits a beam 14. Beam 14 is directed towards the pre-deflector optics 15, which consists of a half wave-plate, a spatial filter and several cylindrical lenses, in order to produce an elliptical beam with a desired polarization that is compatible with the scanner 16. The pre-deflector optics 15 expands the beam 14 to obtain the appropriate numerical aperture. The post-deflector optics 17 includes several cylindrical lenses and an air slit. Finally, the beam 14 is brought into focus on the a wafer surface 12 and scanned along the direction, in the plane of the wafer surface 12, indicated by B, perpendicular to the optical axis of the beam 14. The type of deflector employed in the apparatus is application dependent and may include a polygonal mirror or galvonmeter. However, in the preferred embodiment, deflector 16 is an Acousto-optic Deflector. The wafer surface 12 may be smooth 18 or patterned 19. In addition to the collector channels 10a–b and 11a–b, described above, detector channels are provided which include a reflectivity/autoposition channel 20, an imaging channel 21 and an alignment/registration channel 22, each of which are discussed more fully below.

The beam 14 has a wavelength of 488 nm and is produced by an Argon ion laser. The optical axis 48 of the beam 14 is directed onto the wafer surface 12 at an angle, Θ. This angle, Θ, is in the range of 55–85° with respect to the normal to the wafer surface 12, depending on the application. The scanning means includes the deflector 16 and the translation stage 24 upon which the wafer rests. The position of the wafer on the stage 24 is maintained in any convenient manner, e.g., vacuum suction. The stage 24 moves to partition the surface 12 into striped regions, shown as 25, 26 and 27 with the deflector 16 moving the beam across the width of the striped regions.

Referring to FIG. 2, the grazing angle of the beam 14 produces an elliptical spot 23 on the wafer surface 12, having a major axis perpendicular to the scan line. The deflector 16 scans the spot 23 across a short scan line equal in length to the width of striped region 25 to produce specularly reflected and scattered light. The spot 23 is scanned in the direction indicated, as the stage 24 moves the wafer perpendicular to the scan line. This results in the spot 23 moving within the striped region 25, as shown in FIG. 3. The preferred embodiment scans in only one direction as indicated by scan path 28. Scan path 28 has an effective start location at 29 and the spot 22 moves to the right therefrom until is reaches the border 31 of striped region 25. Upon reaching border 31, the spot 23 the stage 24 moves perpendicular to the scan direction and the spot assumes a new start position 30 and moves parallel to scan line 28, along scan line 32. The deflector 16 continues to scan the spot 23 in this fashion along the entire length of striped region 25. Upon completion of the scan of striped region 25, the stage 24 moves the wafer to permit the scanning of the adjacent striped region 26. The effective start location 33 is positioned so that the stage 24 shall move perpendicular to each scan line in a direction opposite to that when scanning striped region 24, thereby forming a serpentine scan. This is demonstrated by scan paths 34 and 35. Moving the stage 24 to scan adjacent striped regions in opposite directions substantially reduces the amount of mechanical movement of the stage while increasing the number of wafers scanned per hour.

Referring to FIGS. 1 and 3, light scattered from the wafer surface 12 is detected by a plurality of detectors, including collector channels 10a–b and 11a–b. An important aspect of the collector channels is that they collect light over a fixed solid angle, dependent upon, inter alia, the elevational and azimuthal angle of the channel. The optical axis of each collection channel is positioned at an angle of elevation ψ in the range of 70–90 degrees, with respect to the normal to the surface 12. As discussed above collector channels 10a and 10b are symmetrically positioned at the same azimuthal angle with respect to beam 14, on opposite sides of the scan line. Collector channels 10a and 10b are positioned, with respect to the beam 14, at an azimuthal angle $\Phi_1$ in the range of about 75 to about 105 degrees to collect laterally scattered light. Laterally scattered light is defined as light scattered at azimuthal angles in the range of about 75 to about 105 degrees, with respect to beam 14. Similar to collector channels 10a and 10b, channels 11a and 11b are positioned on opposite sides of the scan line at the same azimuthal angle; however, the azimuthal angles $\Phi_2$ of channels 11a and 11b are in the range of 30 to 60 degrees, to collect forwardly scattered light. Forwardly scattered light is defined as light scattered at azimuthal angles in the range of 30 to 60 degrees.

Providing the groups of collector channels, at differing azimuthal angles, facilitates classifying detected anomalies, by taking advantage of a discovery that laterally scattered light is more sensitive to detecting pattern defects, and forwardly scattered light is more sensitive to detecting particulate contaminants. To that end, channels 10a and 10b are positioned to collect laterally scattered light, representing pattern defects, and channels 11a and 11b are provided collect forwardly scattered light, representing particulate contamination.

Referring to FIG. 4, each collector channel 10a–b and 11a–b includes a lens system 113 that collects scattered light. A series of mirrors 114a–c reflect the light so that it is imaged onto a photomultiplier tube (PMT) 115. The PMT 115 converts the light impinging thereon into an electrical signal having a voltage level that is proportional to the light intensity. Positioned at the Fourier transform plane is a programmable spatial filter 116 and a variable aperture stop 117. The programmable spatial filter 116 allows the system to take advantage of spatial filtering when periodic features on the surface 12 are scanned. In addition to the angle of elevation and the azimuthal angle of each channel, the variable aperture stop permits varying the elevational collection angle by limiting the light introduced into the collector channel, in accordance with the geometry of the features on the wafer surface 12. Also located proximate to the Fourier transform plane is a variable polarization filter 118. It should be noted, that it is also possible to place a PMT directly at the Fourier transform plane.

Referring to FIG. 5, it was found that by employing the following polarization schemes, the signal to background of the system could be substantially improved. To obtain optimum signal to background, the polarization scheme employed by the system is surface dependent. It may also be used to determine the composition of the anomaly, e.g., as composed of metallic or dielectric material with respect to pattern defects, the polarizing element included in the post-scanner optics 17 will place the beam 14 in a state of either P or S polarization. A beam is in a state of S polarization when its electrical field is perpendicular to the plane of incidence. The plane of incidence is parallel to the plane of the paper. It is defined by the surface 12, beam 14 and reflected beam 14b. A vector representation of the beam is shown by a $\vec{k}$ vector representing the direction of propagation. The magnetic field is shown as the $\vec{H}$ vector. The electric field vector is shown as being perpendicular to the plane of incidence by representing it with a dot $\vec{E}$. A beam is in a state of P polarization when the electric field is in the plane of incidence. This is shown in FIG. 5B where the beam 14 is shown in vector form with a propagation vector $\vec{k}$, a magnetic field vector shown as a dot $\vec{H}$ and the electric field vector $\vec{E}$, perpendicular to the propagation vector $\vec{k}$. Referring also to FIG. 4, if beam 14 is incident on the surface 12 in an S state of polarization, the variable polarization filter 118 would allow scattered light in an S state of polarization to pass through it and attenuate all other scattered light. For example, both non-polarized or P polarized light would be attenuated and S polarized light would be collected by the collector channels. Alternatively, optimizing the detection of pattern defects could be accomplished with an S polarized beam 14 and the polarization filter allowing all scattered light to pass through it. If the beam 14 is in a P polarization state, the variable polarization filter 118 would allow P polarized light to pass through it and would attenuate all other scattered light. Alternatively, the polarization filter could allow all scattered light to be detected when beam 14 is P polarized. This also optimizes detection of pattern defects. Similarly, if the beam 14 were incident on the surface 12 with either a left or right handed circular polarization, the collector channels would be very sensitive to detecting pattern defects by allowing the polarization filter to pass all the collected light therethrough.

To detect particulate contaminants on a pattern surface, the variable polarization filter 118 would attenuate scattered light that is not in a P state of polarization, if the beam were S polarized. Were beam 14 in a P state of polarization, the collector channels would collect scattered light that was S polarized, whereby the variable polarization filter 118 would attenuate all other scattered light impinging on the channel. For detecting particulates on a bare surface, beam 14 would be in a P state of polarization and the collector channels would collect all light scattered therefrom to maximize the capture rate.

Referring to FIG. 6, an electrical signal 37 is produced by one of the inspection channels corresponding to an intensity I of collected scattered light as a beam scans over a scan path. The abscissa X of the graph in FIG. 5 represents the spatial position of the beam along the scan path. Signal 37 is made of a plurality of discrete samples taken during the scan, e.g., a plurality of scan lines, each of which were scanned at different positions on a surface.

FIGS. 1 and 7A–E is an example of an interchannel communication scheme. Shown therein is a resulting display of a map constructed by a processor 500 from the signals produced by the inspection channels. For purposes of this example, FIGS. 7A and 7B represent scattered light detected by a pair of collector channels. The light detected from the surface consists of a plurality of signals, shown as spots 38. These spots may represent anomalies or false positives: light detected from features or other non-anomalies present on the Surface. The spots 38 may be stored digitally in the processor memory at addresses corresponding to spatial positions on the surface. The processor 500 compares the data stored in memory at addresses represented by the map shown in FIG. 7A with the data stored in memory represented by the map shown in FIG. 7B. The data can be compared by performing various algorithmic or logical operations on it. A logical OR operation maximizes the capture rate at the expense of a potential increase in false counts by storing all anomalies detected between both channels in memory. The composite map shown in FIG. 7C is the end result of performing a logical OR operation on the data stored in the processors memory addresses, as represented by the maps shown in FIGS. 7A and 7B. Alternatively, a logical AND operation would discard all anomalies that are not common to both channels, which is the preferred embodiment. The composite map shown in FIG. 7D is the end result of performing a logical AND operation on the data stored in the processor's memory addresses, as represented by the maps shown in FIGS. 7A and 7B. An exclusive OR operation discards anomalies that are detected on both channels, keeping only those anomalies which are not commonly detected, as shown in FIG. 7E. These "suspect" particles would merit further examination with, inter alia, a high resolution microscope which could be employed on the system.

Referring again to FIG. 6, another manner in which to construct the maps, shown in FIGS. 7A–C, is provided in which only those positions where the signal 37 crosses a certain threshold voltage level are stored in memory, while the remaining signal portions are discarded. For example, two threshold levels are shown: a fixed threshold level 39, and a variable threshold level 40. At threshold level 39, peaks 41–47 are registered and stored in memory. At the variable threshold level 40, as shown, only peaks 41, 43 and 45 are stored in memory. Using the threshold voltage level as shown, fewer positions are registered to form a map thereby making the subsequent processing faster, but at the risk of failing to detect smaller anomalies. The fixed threshold level 39 provides a greater number of positions being detected, but making the system slower. Typically, the fixed threshold level 39 is preset before scanning a wafer, and the variable threshold level is derived from the reflectivity/autoposition channel as described below.

Although the above-described example discussed comparing maps from signals generated by a pair of collector channels, this is not the only manner in which the system may operate. It is to be understood that maps formed from signals generated by the detector channels may also be compared to identify and classify anomalies, by performing algorithms and logical operations on the data, as described above. Comparing signals to a variable threshold level provides an instructive example, because the threshold level is derived from the bright field reflectivity/autoposition channel 20, shown in FIG. 1.

The variable threshold level is dependent upon the local reflectivity. To that end, the bright field reflectivity/autoposition channel 20, is positioned in front of the beam 14 to collect specularly reflected light. The bright field signal derived from this channel carries information concerning the pattern, local variations in reflectivity and height. This channel is sensitive to detecting various defects on a surface. For example, the bright field signal is sensitive to representing film thickness variations, discoloration, stains and local changes in dielectric constant. Taking advantage of bright field signal sensitivity, the bright field signal is used to produce the variable threshold level 40, shown in FIG. 6. It is also used to produce an error height signal, corresponding to a variation in wafer height, which is fed to a z-stage to adjust the height accordingly, as well as to normalize the collector and detection channel signals, whereby the signals from the inspection channels each are divided by the bright field signal. This removes the effect of dc signal changes due to surface variations. Finally, the bright field signal can be used to construct a reflectivity map of the surface. This channel is basically an unfolded Type I confocal microscope operating in reflection mode. It is considered unfolded because the illuminating beam and reflected beams, here, are not collinear, where as, in a typical reflection confocal microscope the illuminating and reflected beams are collinear.

Referring to FIG. 8, the imaging channel is shown to include a lens assembly 119 that images scattered light onto a one-dimensional or two-dimensional array of sensors 120 having pixels, e.g., charge-coupled detectors. The array 120 is positioned so that the pixels collect light scattered by the illuminated spot around directions (e.g. direction 122) normal to the wafer surface 12 with the lens assembly 119 collecting upwardly scattered light. The spot 23 is focused and scanned in synchronism with the transferring of a charge contained in each pixel. This enables charging each pixel 121 independently of the remaining pixels, thereby activating one pixel 122 at a time with each pixel positioned so as to receive light scattered from a unique area of the sample surface, illuminated by the spot along the scan line. In this manner each pixel forms an image on the area illuminated by the spot, wherein there is a one-to-one correlation between a pixel and the spot position along the scan line. This increases the sensitivity of the system by improving the signal to background ratio. For example, it can be shown that for a PMT-based channel, the signal to background is defined as follows:

$$P_s/P_b = \sigma/A_b h$$

where $P_s$ is the optical power scattered by a particle, $P_b$ is the background optical power, $A_b$ is the area of the beam on the surface and $\sigma$ and h are constants. This shows that the ratio of the scattering cross section to the area of the beam determines the signal to background ratio.

With an imaging-based channel, all the scattered power from an anomaly is imaged onto one array element. The power distributed in background, however, is imaged over a range of elements, depending upon the magnification of the system. Assuming a linear magnification M, at the image plane the background power over an area is as follows:

$$M^2 A_b$$

providing an effective background power per array element as $$P_b = P_i h A_c/M^2 A_b$$

where $A_c$ is the area of an array element. Therefore, the signal to background ratio is given by the following:

$$P_s/P_b = M^2 \sigma/A_c h$$

This shows that the signal to background ratio is independent of the spot diameter, providing an improved signal to background ratio given by:

$$i = M^2 A_b/A_c$$

If imaging is not desired, another PMT-based collector channel similar to the one shown in FIG. 4 may be employed in lieu of the imaging channel, to collect upwardly scattered light.

FIG. 9A is a schematic view of an elliptical-shaped illuminated area (or spot) of a surface inspected by the system of this invention to illustrate the invention. As explained, the laser beam illuminating the surface inspected approaches the surface at a grazing angle, so that even though the illumination beam has a generally circular cross-section, the area illuminated is elliptical in shape such as area 210 in FIG. 9A. As known to those skilled in the art, in light beams such as laser beams, the intensity of the light typically does not have a flat distribution and does not fall off abruptly to zero across the boundary of the spot illuminated, such as at boundary 210a of spot 210 of FIG. 9A. Instead, the intensity falls off at the outer edge of the illuminated spot at a certain inclined slope, so that instead of sharp boundaries such as boundary 210a illustrated in FIG. 9A, the boundary is typically blurred and forms a band of decreasing intensity at increasing distance away from the center of the illuminated area.

In many lasers, the laser beam produced has a Gaussian intensity distribution, such as that shown in FIG. 9B. FIG. 9B is a graphical illustration of the spatial distribution of the illumination intensity in the Y direction of a laser beam that is used in the preferred embodiment to illuminate spot 210 of a surface to be inspected as shown in FIG. 9A, and thus is also the illumination intensity distribution across spot 10 in the Y direction. As shown in FIG. 9B, the illumination intensity has been normalized so that the peak intensity is 1, and the illumination intensity has a Gaussian distribution in the X direction as well as in the Y direction. Points 212 and 214 are at spatial locations y1 and y5 at which points the illumination intensity drops to $1/e^2$ of the peak intensity, where e is the natural number. The spot 210 is defined by the area within a boundary 10a where the illumination is $1/e^2$ of that of the maximum intensity of illumination at the center of the spot. The lateral extent of the spot 210 may then be defined to be the boundary 210a. The size of the spot is then defined by means of the boundary obviously, other definitions of the boundary of a spot and of spot size are possible, and the invention herein is not restricted to the above definition.

To maintain uniform detection sensitivity, the scanning light beam is preferably caused to scan short sweeps having a spatial span less than the dimension of the surface it is scanning, as illustrated in the preferred embodiment in FIG. 10, where these short sweeps are not connected together but are located so that they form arrays of sweeps. Preferably, the lengths of the sweeps are in the range of 2–25 mm.

The surface inspection system of this application will now be described with reference to FIGS. 1 and 10. As shown in FIG. 10, system 200 includes a laser 222 providing a laser beam 224. Beam 224 is expanded by beam expander 226 and the expanded beam 228 is deflected by acousto-optic deflector (AOD) 230 into a deflected beam 232. The deflected beam 232 is passed through post-AOD and polarization selection optics 234 and the resulting beam is focused by telecentric scan lens 236 onto a spot 210 on surface 240 to be inspected, such as that of a semiconductor wafer, photomask or ceramic tile, patterned or unpatterned.

In order to move the illuminated area that is focused onto surface 240 for scanning the entire surface, the AOD 230 causes the deflected beam 232 to change in direction, thereby causing the illuminated spot 210 on surface 240 to be scanned along a sweep 250. As shown in FIG. 10, sweep 250 is preferably a straight line having a length which is smaller than the dimension of surface 240 along the same direction as the sweep. Even where sweep 250 is curved, its span is less than the dimension of surface 240 along the same general direction. After the illuminated spot has traversed along sweep 250, surface 240 of the wafer is moved by XY stage 24 (FIG. 1) parallel to the X axis in FIG. 10 so that the illuminated area of the surface moves along arrow 252 and AOD 230 causes the illuminated spot to scan a sweep 250' parallel to sweep 250 and in an adjacent position spaced apart from sweep 250 along the X axis to scan an adjacent sweep at a different X position. As described below, this small distance is preferably equal to about one quarter of the dimension of spot 210 in the X direction. This process is repeated until the illuminated spot has covered strip 254; at this point in time the illuminated area is at or close to the edge 254a. At such point, the surface 240 is moved by XY stage 24 along the Y direction by about the length of sweep 250 in order to scan and cover an adjacent strip 256, beginning at a position at or close to edge 256a. The surface in strip 256 is then covered by short sweeps such as 250 in a similar manner until the other end or edge 256b of strip 256 is reached at which point surface 240 is again moved along the Y direction for scanning strip 258. This process is repeated prior to the scanning of strip 254, 256, 258 and continues after the scanning of such strips until preferably the entire surface 240 is scanned. Surface 240 is therefore scanned by scanning a plurality of arrays of sweeps the totality of which substantially covers the entire surface 240.

The deflection of beam 232 by AOD 230 is controlled by chirp generator 280 which generates a chirp signal. The chirp signal is amplified by amplifier 282 and applied to the transducer portion of AOD 230 for generating sound waves to cause deflection of beam 232 in a manner known to those skilled in the art. For a detailed description of the operation of the AOD, see "Acoustooptic Scanners and modulators," by Milton Gottlieb in *Optical Scanning*, ed. by Gerald F. Marshall, Dekker 1991, pp. 615–685. Briefly, the sound waves generated by the transducer portion of AOD 230 modulate the optical refractive index of an acoustooptic crystal in a periodic fashion thereby leading to deflection of beam 232. Chirp generator 280 generates appropriate signals so that after being focused by lens 236, the deflection of beam 232 causes the focused beam to scan along a sweep such as sweep 250 in the manner described.

Chirp generator 280 is controlled by timing electronics circuit 284 which in the preferred embodiment includes a microprocessor. The microprocessor supplies the beginning and end frequencies f1, f2 to the chirp generator 280 for generating appropriate chirp signals to cause the deflection of beam 232 within a predetermined range of deflection angles determined by the frequencies f1, f2. The illumination sensor optics 20 and adaptive illumination control 292 are used to detect and control the level of illumination of spot 210. The optics 20 and adaptive illumination control 292 are explained in detail in U.S. Pat. No. 5,530,550.

Detectors such as detectors 10a, 10b, 11a, 11b of FIGS. 1 and 10 collect light scattered by anomalies as well as the surface and other structures thereon along sweeps such as sweep 250 and provide output-signals to processor 500 in order to detect anomalies and analyze their characteristics.

FIG. 9C is a schematic view of three positions of the illuminated area or spot on a surface to be inspected to illustrate the scanning and data gathering process of system 200. As shown in FIG. 9C, at one instant in time, beam 238 illuminates an area 210 on surface 240. Spot 210 is divided into sixteen areas by grid lines x1–x5, y1–y5, where such areas are referred to below as pixels. In this context, the term "pixel" is defined by reference to the taking of data samples across the intensity distributions along the X and Y axes, such as that in FIG. 9C, and by reference to subsequent data processing. The pixel that is bounded by grid lines x2, x3 and y2, y3 is pixel P shown as a shaded area in FIG. 9C. If there is an anomaly in this pixel P, and if the light illuminating pixel P has the intensity distribution as shown in FIG. 9B with a high intensity level between grid lines y2 and y3, light scattered by the anomaly will also have a high intensity. However, as the beam moves along the Y axis so that the area 210' is illuminated instead, pixel P will still be illuminated but at the lower intensity level of that between grid lines y1 and y2; in reference to FIG. 9B, the intensity of the illumination is that between grid lines y1 and y2 in FIG. 9B. Therefore, if the sampling rate employed by the data processor 500 in FIGS. 1 and 10 for processing light detected by the collection or collector channels 10a, 10b, 11a, 11b is such that a data sample is taken when the illuminating beam is in position 210 and when the illuminating beam is in position 210', then two data samples will be recorded. Thus, for any pixel such as P, a number of data points will be taken, one when the illumination is at a higher level as illustrated by data point D2 in FIG. 9B and another one when the illumination is at a lower level, illustrated at data point D1 in FIG. 9B. If position 210 is not the starting position of the sweep 250, then two prior samples would have been taken prior to the time when the illuminating beam illuminates the surface 240 in position 210, so that the processor would have obtained two more data samples at points D3, D4 corresponding to the prior positions of the illuminating beam when light of intensity values between grid lines y3, y4 and between y4, y5 respectively illuminates such pixel P (grid lines y1 through y5 would, of course, move with the location of the spot). In other words, four separate data samples at points D1–D4 would have been taken of the light scattered by an anomaly present in pixel P as the illumination beam illuminates pixel P when scanning along the Y direction.

In most laser beams, the beam intensity has a Gaussian intensity distribution not only in the Y direction but also in the X direction. For this reason, after the illuminating beam completes the scanning operation for scanning a sweep such as sweep 250 as shown in FIG. 10, and when the illuminating beam returns to position 274 for scanning the adjacent sweep 253 as shown in FIG. 10, it is desirable for the illuminated area along sweep 250' to overlap that of sweep 250 so that multiple samples or data points can again be taken also along the X direction as well as along the Y direction. Therefore, when the illumination beam is scanning along sweep 250' from starting position 274 as shown in FIG. 10, the area illuminated would overlap spot 210; this overlapping spot is 210" as shown in FIG. 9C, where the spot 210" is displaced along the X direction relative to spot 210 by one quarter of the long axis of the ellipses 210 and 210".

Detector 120 includes a one-dimensional or two-dimensional array of sensors. To enable time delayed integration as described below, detector 120 employs a two-dimensional array of sensors as illustrated in FIG. 11.

In reference to FIGS. 8 and 9C, in the preferred embodiment, the lens assembly 119 focuses the light scattered from only a portion of the illuminated spot 210 to a corresponding sensor in a two-dimensional array of sensors 120. By focusing the light scattered by only a portion of the illuminated spot onto a sensor, the sensitivity of the detection system of FIG. 8 is enhanced as compared to a system where light scattered by the entire spot is focused to a sensor. In the preferred embodiment, the lens assembly 119 focuses the light scattered from a pixel, such as pixel P, towards a corresponding sensor in the array 120. As noted above, each pixel on the surface inspected will be illuminated four times in four adjacent and consecutive scans along the Y axis. Thus, in regard to pixel P, it was illuminated during the scan prior to the sweep 250, during sweep 250, during sweep 250' and the sweep subsequent to sweep 250'. Furthermore, the focusing of light from only a portion of the spot to a sensor also enables time delay integration to be carried out to enhance the signal-to-ratio in a manner described below.

For the purpose of illustration, it is assumed that when spot 210 is scanned along the sweep immediately prior to sweep 250, light scattered from the pixel P is focused by lens assembly 119 onto sensor 121(1)(3) of detector 120 in FIG. 11. Light scattered by pixels adjacent to and having the same Y coordinates as P will be focused by assembly 119 to other sensors in the linear array or line 121(1) of sensors in FIG. 11. In order for the spot 210 to be then subsequently scanned along sweep 250, XY stage 24 moves the wafer surface by a distance substantially equal to ¼ of the length of the long axis of spot 210, so that the lens assembly 119 will now focus the light scattered by pixel P onto sensor 121(2)(3) instead of 121(1)(3), and light scattered by P's adjacent pixels and with the same Y coordinates to sensors along line 121(2). As shown in FIG. 11, sensor 121(1)(3) is electrically connected to sensor 121(2)(3) (e.g. by a wire); in the same vein, the remaining sensors in line 121(1) are similarly electrically connected to corresponding sensors in line 121 (2) as shown in FIG. 11. Similarly, the sensors in line 121(2) are electrically connected to corresponding sensors in line 121(3) and so on for all adjacent pairs of lines of sensors in detector 120.

To enable time delayed integration, processor 500 causes the signal in sensor 121(1)(3) obtained by detecting light scattered by pixel P during the previously described scan to be transferred to sensor 121(2)(3), so that the signal obtained during the prior scan will be added to that obtained by sensor 121(2)(3) from detecting the light scattered by pixel P during sweep 250. Similarly, processor 500 causes the thus accumulated signal in sensor 121(2)(3) to be transferred to sensor 121(3)(3) prior to the sweep 250', so that the signal thus accumulated can be added to that obtained by sensor 121 (3)(3) by detecting the light scattered from pixel P during sweep 250'. In this manner, time delayed integration is performed by accumulating the signals obtained from light scattering from pixel P during four sequential sweeps and is read out as the output signal for such pixel. The same can be done for other pixels on the surface of the wafer. While in the preferred embodiment, the amount of overlap and the sampling rate are controlled so that each illuminating spot is divided into 16 pixels, it will be understood that the spot may be divided into a smaller or greater number of pixels by altering the amount of overlap between sequential sweeps and by altering the sampling rate; such and other variations are within the scope of the invention.

The above-described process may be performed for all of the pixels in the illuminated spot where processor 500 simply causes all of the signals in each linear array or line of sensors, such as line 121(1) to be transferred to corresponding sensors in the next line 121(2), and this process is carried out for all of the lines, from line 121(1) to the next to the last line 121(N-1), so that time delay integration is performed for all of the pixels. The number of sensors in each line is preferably large enough to cover all the pixels in each sweep. In order to avoid edge effects, it may be desirable to include enough lines of sensors to cover all of the possible positions of the pixels in the illuminated spot along the X direction of the wafer.

As described above, signals obtained by light scattering from the pixel are accumulated over four sequential sweeps. The final accumulated signal is then read but by processor 500 as the output of detector 120 for such pixel. Processor 500 then constructs a defect map from a two-dimensional array of such accumulate signals from the outputs of detector 120. Such map may be compared to the defect maps obtained by processor 500 from detectors 10a, 10b, 11a and 11b to obtain an AND, a union and an XOR map for the purpose of identifying anomalies. Thus, an AND map would comprise only of anomalies present in a map from one detector and in a map or maps from one or more of the remaining detectors. A union map comprises of anomalies present in at least one of the maps of two or more detectors. An XOR map comprises of anomalies present in the map of only one detector but not in the map or maps of the remaining detectors. As noted above, the above maps are useful for classifying defects. Thus, if an anomaly is present in the map of one detector but not in the map of the other symmetrically placed detector, then the anomaly is probably not symmetrical. Or if an anomaly is present in the map of detectors 10a, 10b for detecting laterally scattered light but not in the maps of detectors 11a, 11b for detecting forward scattered light, then the anomaly may be more likely to be a pattern defect than a particle.

The XY stage 24 is controlled by a controller (not shown) in communication with processor 500. As this controller causes the stage 24 to move the wafer by a quarter of the X dimension of the spot 210, this is communicated to processor 500, which sends control signals to detector 120 to cause a transfer of signals between adjacent lines of sensors and sends control signals to timing electronics 284 as shown in FIG. 10. Electronics 284 in turn controls the chirp rate of chirp generator 280 so that the transfer of signals between adjacent lines of sensors in detector 120 will have occurred prior to the scanning of the illuminated spot.

In the preferred embodiment, the illuminated spot has a spot size whose minimum dimension is in the range of about 2 to 25 microns.

Referring again to FIG. 1, an alignment and registration channel 22 is provided. Instead of the design in FIGS. 8 and 11, the channel 21 may also have the same design as a basic collection channel 10a, 10b and 11a, 11b, but it is positioned in the plane of incidence so that the signal produced from the patterns or features on the wafer's surface is at a maximum. The signal obtained is used to properly align the wafer surface 12 so that the streets on the features are not oblique with the scan line. This also reduces the amount of signal collected by the collector channels, resulting from scattering by patterns.

In operation, the beam 14 is scanned over the surface 12, producing both scattered and specularly reflected light, which are simultaneously detected. The light scattered laterally, forwardly and upwardly is simultaneously detected by the collector channels and the imaging system. The specularly reflected light from the wafer's surface 12 is detected by the bright field reflectivity/autoposition channel 20. Light detected by the inspection channels is converted into electrical signals which are further processed by dedicated electronics, including a processor 500. The processor 500 constructs maps from the signals produced by the inspection channels. When a plurality of identical dies are present on the wafer surface 12, a detection method may be employed whereby periodic feature comparisons are made between adjacent die. The processor compares the maps from the inspection channels either in the analog domain or digitally, by performing logical operations on the data, e.g., AND, OR and XOR, in the manner described above, to detect anomalies. The processor forms composite maps, each representing the detected anomalies by a single group of symmetrically disposed collector channels. The composite maps are then compared so that the processor may classify the anomalies as either a pattern defect or particulate contamination. Typically, the wafer surface 12 has been aligned so that the streets on the die are not oblique with respect to the scan line, using the information carried by the electrical signal produced by the alignment/registration channel. Proper alignment is a critical feature of this invention, because periodic feature comparison is performed to locate anomalies.

While the above described apparatus and method for detecting anomalies has been described with reference to a wafer surface, it can easily be seen that anomaly detection is also possible for photomasks and other surfaces, as well as producing reflectivity maps of these surfaces. The invention is capable of detecting anomalies of submicron size and affords the added advantage of classifying the type of anomaly and identifying its size and position on the surface. This information is highly useful to wafer manufacturers as it will permit locating the step in the wafer manufacturing process at which point an anomaly occurs.

What is claimed is:

1. An optical scanning system for detection of anomalies on a surface comprising:
   optics directing a focused beam of radiation onto a sample surface to produce an illuminated spot thereon;
   one or more sensors;
   one or more optical elements, each element collecting radiation scattered from the illuminated spot on the surface along a channel away from a specular reflection direction of the beam and directing the collected and scattered radiation to one of the sensors, causing each of the sensors to provide output signals in response thereto;
   a detector; and
   a device causing relative motion between the beam and the surface so that the beam is caused to illuminate different parts of the surface and so that the sensors and the detector provide output signals in response to radiation from different parts of the surface illuminated by the beam, said detector performing time delayed integration on signals provided in response to radiation from the illuminated spot on the surface in synchronism with the relative motion to provide output signals.

2. The system of claim 1, said system comprising a two dimensional array of detectors, each of at least some of said detectors providing output signals in response to the collected scattered light from each of portions in an array of surface portions in the illuminated spot defining a line of pixels.

3. The system of claim 2, said relative motion causing the beam to scan a first line of pixels in a first scan and a second line of pixels in a subsequent second scan, each of said optical element(s) focusing radiation from at least some of the pixels in the line of pixels to a first line of detectors during the first scan and to a second line of detectors during the second scan, said system further comprising a processor transferring output signals from the first line of detectors to the second line of detectors to perform time delayed integration.

4. The system of claim 1, wherein the beam illuminates an elongated spot on the surface, said detector comprising a time delayed integration camera.

5. The system of claim 1, wherein said detector detects radiation scattered from the illuminated spat on the surface.

6. The system of claim 1, said system comprising three or more sensors and three or more optical elements, said channels disposed about a circumference of the surface so that each of the sensors sense radiation scattered from the surface in directions different from those of radiation sensed by the other sensor(s).

7. The system of claim 1, said device comprising an acousto-optic deflector.

8. The system of claim 1, further comprising a confocal optical detection channel.

9. The system of claim 1, further comprising a polarization element that causes the beam to be polarized.

10. The system of claim 9, further comprising a variable polarization filter in at least one of the channels.

11. The system of claim 1, further comprising a spatial filter.

12. The system of claim 11, wherein said spatial filter is programmable.

13. The system of claim 1, said system comprising two or more sensors and two or more optical elements, each element collecting radiation scattered from the illuminated spot on the surface along a channel and directing the collected and scattered radiation to one of the sensors, causing each of the sensors to provide output signals in response thereto, each of the sensors sensing radiation scattered from the surface in directions away from a specular reflection direction and different from those of radiation sensed by the other sensor(s), said system further comprising:
   a storage component storing data corresponding to output signals provided by at least two of said sensors in response to scattered radiation from the spot scanned across the surface; and
   a processor comparing data corresponding to output signals provided by one of the at least two sensors in response to scattered radiation from the spot scanned across the surface to data corresponding to output signals provided by another one of the at least two sensors in response to scattered radiation from the spot scanned across the surface.

14. The system of claim 13, wherein said processor compares the data to identify and/or classify anomalies.

15. The system of claim 1, said system comprising two or more sensors; said system further comprising:
   a detection channel detecting radiation in the beam from the illuminated spot on the surface to provide an output signal; and
   a processor processing output signals provided by said sensors, wherein said processor derives one or more threshold level values for processing the output signals provided by said sensors from an output of the detection channel.

16. The system of claim 15, wherein said one or more threshold level values comprises at least one variable threshold level value.

17. The system of claim 15, said detection channel comprising a bright field detector detecting a specular reflection of the radiation in the beam from the illuminated spot on the surface.

18. The system of claim 1, said system comprising an autoposition detection channel.

19. The system of claim 1, said system comprising a confocal detection channel.

20. The system of claim 1, said device causing the beam to scan a serpentine path on the surface.

21. The system of claim 1, said device causing the beam to scan a path on the surface, said system further comprising a registration detection channel that provides a signal for aligning the path with streets on the surface.

22. The system of claim 1, wherein said relative motion between the beam and the surface causes the beam to scan a scan path covering at least a portion of the surface, said path comprising a plurality of scan path segments, wherein each of at least some of such scan path segments has a span shorter than the dimensions of the surface.

23. The system of claim 22, wherein some of said scan path segments form an array.

24. The system of claim 1, wherein said beam of radiation is incident onto the sample surface at an oblique angle.

25. The system of claim 1, wherein said beam of radiation is incident onto the sample surface at a grazing angle.

26. The system of claim 1, wherein said relative motion causes the illuminated spot to scan along adjacent scan path segments on the surface, wherein the adjacent scan path segments overlap.

27. The system of claim 1, wherein said sensors are positioned symmetrically in the azimuth.

28. The system of claim 1, said system comprising an imaging detection channel detecting radiation scattered from the illuminated spot on the surface, said imaging channel comprising a photomultiplier tube or a two dimensional detector array performing time delayed integration.

29. An optical scanning system for detection of anomalies on a surface comprising:
   directing a focused beam of radiation onto a sample surface to produce an illuminated spot thereon;
   collecting radiation scattered from the illuminated spot on the surface along one or more channels away from a specular reflection direction of the beam and directing the collected and scattered radiation to one or more sensors, causing each of the sensors to provide output signals in response thereto;
   causing relative motion between the beam and the surface so that the beam is caused to illuminate different parts of the surface and so that the sensors and a detector provide output signals in response to radiation from different parts of the surface illuminated by the beam; and
   causing said detector to perform time delayed integration on signals provided in response to radiation from the illuminated spot on the surface in synchronism with the relative motion to provide output signals.

30. The method of claim 29, wherein said causing to perform time delayed integration causes each of at least some of detectors in a two dimensional array of detectors to provide output signals in response to the collected scattered light from each of portions in an array of surface portions in the illuminated spot defining a line of pixels.

31. The system of claim 30, said relative motion causing the beam to scan a first line of pixels in a first scan and a second line of pixels in a subsequent second scan, wherein said causing comprises focusing radiation from at least some of the pixels in the line of pixels to a first line of detectors during the first scan and to a second line of detectors during the second scan, said method further comprising transferring output signals from the first line of detectors to the second line of detectors to perform time delayed integration.

32. The system of claim 29, wherein directing directs the beam to illuminate an elongated spot on the surface.

33. The method of claim 29, further comprising polarizing the beam.

34. The method of claim 33, wherein said polarizing polarizes the beam so that it has S, P or circular polarization.

35. The method of claim 34, wherein said collecting collects radiation of all polarization.

36. The method of claim 33, wherein said polarizing polarizes the beam so that it has S polarization and said collecting collects radiation of S polarization.

37. The method of claim 33, wherein said polarizing polarizes the beam so that it has P polarization and said collecting collects radiation of P polarization.

38. The method of claim 33, wherein said polarizing polarizes the beam so that it has S or P polarization and said collecting collects radiation of all polarization.

39. The method of claim 33, wherein said collecting and directing direct collected radiation to two or more sensors, said method further comprising:
   storing data corresponding to output signals provided by at least two of the said sensors in response to scattered radiation from the spot scanned across the surface; and
   comparing data corresponding to output signals provided by one of the at least two of the said sensor in response to scattered radiation from the spot scanned across the surface to data corresponding to output signals provided by another one of the at least two of the said sensor in response to scattered radiation from the spot scanned across the surface.

40. The method of claim 39, wherein said comparing compares the data to identify and/or classify anomalies.

41. The method of claim 29, said method further comprising:
   detecting radiation in the beam from the illuminated spot on the surface by means of a detection channel to provide an output signal; and
   processing the output signals of the sensors, wherein said processing derives one or more threshold level values for processing the output signals provided by said sensors from an output of the detection channel.

42. The system of claim 41, wherein said one or more threshold level values comprises at least one variable threshold level value.

43. The method of claim 41, wherein said detecting detects a specular reflection of the radiation in the beam from the illuminated spot on the surface.

44. The method of claim 29, wherein said relative motion causing causes the beam to scan a serpentine path on the surface.

45. The method of claim 29, wherein said relative motion causing causes the beam to scan a path on the surface, said method further comprising aligning the path with streets on the surface.

46. The method of claim 29, wherein said relative motion between the beam and the surface causes the beam to scan a scan path covering at least a portion of the surface, said path comprising a plurality of scan path segments, wherein each of at least some of such scan path segments has a span shorter than the dimensions of the surface.

47. The method of claim 46, wherein some of said scan path segments form an array.

48. The method of claim 29, wherein said beam of radiation is incident onto the sample surface at an oblique angle.

49. The method of claim 29, wherein said beam of radiation is incident onto the sample surface at a grazing angle.

50. The method of claim 29 wherein said relative motion causes the illuminated spot to scan along adjacent scan path segments on the surface, wherein the adjacent scan path segments overlap.

51. The method of claim 29, wherein said collecting and directing directs collected radiation to three or more sensors by means of three or more optical elements, said channels disposed about a circumference of the surface so that each of the sensors sense radiation scattered from the surface in directions different from those of radiation sensed by the other sensor(s).

52. An optical scanning system for detection of anomalies on a surface comprising:
- optics directing a focused beam of radiation onto a sample surface to produce an illuminated spot thereon;
- a detector; and
- a device causing relative motion between the beam and the surface so that the beam is caused to illuminate different parts of the surface and so that the detector provides output signals in response to radiation from different parts of the surface illuminated by the beam, said detector performing time delayed integration on signals provided in response to radiation from the illuminated spot on the surface in synchronism with the relative motion to provide output signals, said device comprising an acousto-optic deflector.

53. The system of claim 52, said system comprising a two dimensional array of detectors, each of at least some of said detectors providing output signals in response to the collected scattered light from each of portions in an array of surface portions in the illuminated spot defining a line of pixels.

54. The system of claim 53, said relative motion causing the beam to scan a first line of pixels in a first scan and a second line of pixels in a subsequent second scan, each of said optical element(s) focusing radiation from at least some of the pixels in the line of pixels to a first line of detectors during the first scan and to a second line of detectors during the second scan, said system further comprising a processor transferring output signals from the first line of detectors to the second line of detectors to perform time delayed integration.

55. The system of claim 52, wherein the beam illuminates an elongated spot on the surface, said detector comprising a time delayed integration camera.

56. The system of claim 52, wherein said detector detects radiation scattered from the illuminated spot on the surface away from a specular reflection direction of the beam.

57. The system of claim 52, further comprising:
- one or more sensors; and
- one or more optical elements, each element collecting radiation scattered from the illuminated spot on the surface along one or more channels away from a specular reflection direction of the beam and directing the collected and scattered radiation to one of the sensors, causing each of the sensors to provide output signals in response thereto.

58. The system of claim 52, said device comprising an acousto-optic deflector.

59. The system of claim 52, wherein said detector detects radiation scattered from the illuminated spot on the surface away from a specular reflection of the beam.

60. The system of claim 52, said system further comprising:
- two or more sensors;
- two or more optical elements, each element collecting radiation scattered from the illuminated spot on the surface along a channel and directing the collected and scattered radiation to one of the sensors, causing each of the sensors to provide output signals in response thereto, each of the sensors sensing radiation scattered from the surface in directions away from a specular reflection direction and different from those of radiation sensed by the other sensor(s).

61. The system of claim 60, said system comprising:
- three or more sensors and three or more optical elements, said channels disposed about a circumference of the surface so that each of the sensors sense radiation scattered from the surface in directions different from those of radiation sensed by the other sensor(s).

62. The system of claim 52, said device comprising an acousto-optic deflector.

63. The system of claim 52, further comprising a confocal optical detection channel.

64. The system of claim 52, further comprising a polarization element that causes the beam to be polarized.

65. The system of claim 64, further comprising a variable polarization filter in at least one of the channels.

66. The system of claim 52, further comprising a spatial filter.

67. The system of claim 66, wherein said spatial filter is programmable.

68. The system of claim 52, said system further comprising:
- two or more sensors and two or more optical elements, each element collecting radiation scattered from the illuminated spot on the surface along a channel and directing the collected and scattered radiation to one of the sensors, causing each of the sensors to provide output signals in response thereto, each of the sensors sensing radiation scattered from the surface in directions away from a specular reflection direction and different from those of radiation sensed by the other sensor(s);
- a storage component storing data corresponding to output signals provided by at least two of said sensors in response to scattered radiation from the spot scanned across the surface; and
- a processor comparing data corresponding to output signals provided by one of the at least two sensors in response to scattered radiation from the spot scanned across the surface to data corresponding to output signals provided by another one of the at least two sensors in response to scattered radiation from the spot scanned across the surface.

69. The system of claim 68, wherein said processor compares the data to identify and/or classify anomalies.

70. The system of claim 52, said system further comprising:
- two or more sensors;
- a detection channel detecting radiation in the beam from the illuminated spot on the surface to provide an output signal; and
- a processor processing output signals provided by said sensors, wherein said processor derives one or more threshold level values for processing the output signals provided by said sensors from an output of the detection channel.

71. The system of claim 70, wherein said one or more threshold level values comprises at least one variable threshold level value.

72. The system of claim 70, said detection channel comprising a bright field detector detecting a specular reflection of the radiation in the beam from the illuminated spot on the surface.

73. The system of claim 52, said system comprising an autoposition detection channel.

74. The system of claim 52, said system comprising a confocal detection channel.

75. The system of claim 52, said device causing the beam to scan a serpentine path on the surface.

76. The system of claim 52, said device causing the beam to scan a path on the surface, said system further comprising a registration detection channel that provides a signal for aligning the path with streets on the surface.

77. The system of claim 52, wherein said relative motion between the beam and the surface causes the beam to scan a scan path covering at least a portion of the surface, said path comprising a plurality of scan path segments, wherein each of at least some of such scan path segments has a span shorter than the dimensions of the surface.

78. The system of claim 77, wherein some of said scan path segments form an array.

79. The system of claim 52, wherein said beam of radiation is incident onto the sample surface at an oblique angle.

80. The system of claim 52, wherein said beam of radiation is incident onto the sample surface at a grazing angle.

81. The system of claim 52, wherein said relative motion causes the illuminated spot to scan along adjacent scan path segments on the surface, wherein the adjacent scan path segments overlap.

82. The system of claim 52, said system further comprising:

two or more sensors and two or more optical elements, each element collecting radiation scattered from the illuminated spot on the surface along a channel and directing the collected and scattered radiation to one of the sensors, causing each of the sensors to provide output signals in response thereto, each of the sensors sensing radiation scattered from the surface in directions away from a specular reflection direction and different from those of radiation sensed by the other sensor(s), wherein said sensors are positioned symmetrically in the azimuth.

83. The system of claim 52, said system comprising an imaging detection channel detecting radiation scattered from the illuminated spot on the surface, said imaging channel comprising a photomultiplier tube or a two dimensional detector array performing time delayed integration.

84. The system of claim 52, further comprising a bright field detector.

85. The system of claim 84, said bright field detector comprising a detection element and an optical element that focuses radiation from the illuminated spot to the detection element.

86. An optical scanning method for detection of anomalies on a surface comprising:

directing a focused beam of radiation onto a sample surface to produce an illuminated spot thereon;

causing relative motion between the beam and the surface by means of an acousto-optic deflector so that the beam is caused to illuminate different parts of the surface; and causing the detector to perform time delayed integration in response to radiation from the illuminated spot on the surface in synchronism with the relative motion to provide output signals, said device comprising.

87. The method of claim 86, wherein said causing to perform time delayed integration causes each of at least some of detectors in a two dimensional array of detectors to provide output signals in response to the collected scattered light from each of portions in an array of surface portions in the illuminated spot defining a line of pixels.

88. The system of claim 87, said relative motion causing the beam to scan a first line of pixels in a first scan and a second line of pixels in a subsequent second scan, wherein said causing comprises focusing radiation from at least some of the pixels in the line of pixels to a first line of detectors during the first scan and to a second line of detectors during the second scan, said method further comprising transferring output signals from the first line of detectors to the second line of detectors to perform time delayed integration.

89. The system of claim 86, wherein directing directs the beam to illuminate an elongated spot on the surface.

90. The method of claim 86, comprising polarizing the beam.

91. The method of claim 90, wherein said polarizing polarizes the beam so that it has S, P or circular polarization.

92. The method of claim 91, wherein said collecting collects radiation of all polarization.

93. The method of claim 90, wherein said polarizing polarizes the beam so that it has S polarization and said collecting collects radiation of S polarization.

94. The method of claim 90, wherein said polarizing polarizes the beam so that it has P polarization and said collecting collects radiation of P polarization.

95. The method of claim 90, wherein said polarizing polarizes the beam so that it has S or P polarization and said collecting collects radiation of all polarization.

96. The method of claim 90 further comprising:

collecting radiation scattered from the illuminated spot on the surface along channels away from a specular reflection direction of the beam and directing the collected and scattered radiation to two or more sensors, causing each of the sensors to provide output signals in response thereto;

storing data corresponding to output signals provided by at least two of the said sensors in response to scattered radiation from the spot scanned across the surface; and comparing data corresponding to output signals provided by one of the at least two of the said sensor in response to scattered radiation from the spot scanned across the surface to data corresponding to output signals provided by another one of the at least two of the said sensor in response to scattered radiation from the spot scanned across the surface.

97. The method of claim 96, wherein said comparing compares the data to identify and/or classify anomalies.

98. The method of claim 90, said method further comprising:

collecting radiation scattered from the illuminated spot on the surface along channels away from a specular reflection direction of the beam and directing the collected and scattered radiation to two or more sensors, causing each of the sensors to provide output signals in response thereto;

detecting radiation in the beam from the illuminated spot on the surface by means of a detection channel to provide an output signal; and processing the output signals of the sensors, wherein said processing derives one or more threshold level values for processing die output signals provided by said sensors from an output of the detection channel.

99. The system of claim 98, wherein said one or more threshold level values comprises at least one variable threshold level value.

100. The method of claim 98, wherein said detecting detects a specular reflection of the radiation in the beam from the illuminated spot on the surface.

101. The method of claim 90, wherein said relative motion causes the beam to scan a serpentine path on the surface.

102. The method of claim 90, wherein said relative motion causes the beam to scan a path on the surface, said method further comprising aligning the path with streets on the surface.

103. The method of claim 90, wherein said relative motion between the beam and the surface causes the beam to scan a scan path covering at least a portion of the surface, said path comprising a plurality of scan path segments, wherein each of at least some of such scan path segments has a span shorter than the dimensions of the surface.

104. The method of claim 103, wherein some of said scan path segments form an array.

105. The method of claim 90, wherein said beam of radiation is incident onto the sample surface at an oblique angle.

106. The method of claim 90, wherein said beam of radiation is incident onto the sample surface at a grazing angle.

107. The method of claim 90, wherein said relative motion causes the illuminated spot to scan along adjacent scan path segments on the surface, wherein the adjacent scan path segments overlap.

108. The method of claim 90, said method further comprising:
collecting radiation scattered from the illuminated spot on the surface along channels away from a specular reflection direction of the beam and directing the collected and scattered radiation to three or more sensors, causing each of the sensors to provide output signals in response thereto;
said channels disposed about a circumference of the surface so that each of the sensors sense radiation scattered from the surface in directions different from those of radiation sensed by the other sensor(s).

109. An optical scanning system for detection of anomalies on a surface comprising:
optics directing a focused beam of radiation onto a sample surface to produce an illuminated spot thereon;
a confocal sensor,
a detector; and
a device causing relative motion between the beam and the surface so that the beam is caused to illuminate different parts of the surface and so that the detector and sensor provide output signals in response to radiation from different parts of the surface illuminated by the beam, said detector performing time delayed integration on signals provided in response to radiation from the illuminated spot on the surface in synchronism with the relative motion to provide output signals.

110. The system of claim 109, said sensor comprising a two dimensional array of detectors, each of at least some of said detectors providing output signals in response to the collected scattered light from each of portions in an array of surface portions in the illuminated spot defining a line of pixels.

111. The system of claim 110, said relative motion causing the beam to scan a first line of pixels in a first scan and a second line of pixels in a subsequent second scan, each of said optical element(s) focusing radiation from at least some of the pixels in the line of pixels to a first line of detectors during the first scan and to a second line of detectors during the second scan, said system further comprising a processor transferring output signals from the first line of detectors to the second line of detectors to perform time delayed integration.

112. The system of claim 109, wherein the beam illuminates an elongated spot on the surface, said detector comprising a time delayed integration camera.

113. The system of claim 109, wherein said detector detects radiation scattered from the illuminated spot on the surface away from a specular reflection direction of the beam.

114. The system of claim 109, further comprising:
one or more sensors; and
one or more optical elements, each element collecting radiation scattered from the illuminated spot on the surface along one or more channels away from a specular reflection direction of the beam and directing the collected and scattered radiation to one of the sensors, causing each of the sensors to provide output signals in response thereto.

115. The system of claim 109, said device comprising an acousto-optic deflector.

116. The system of claim 109, wherein said detector detects radiation scattered from the illuminated spot on the surface away from a specular reflection of the beam.

117. The system of claim 109, said system further comprising:
two or more sensors;
two or more optical elements, each element collecting radiation scattered from the illuminated spot on the surface along a channel and directing the collected and scattered radiation to one of the sensors, causing each of the sensors to provide output signals in response thereto, each of the sensors sensing radiation scattered from the surface in directions away from a specular reflection direction and different from those of radiation sensed by the other sensor(s).

118. The system of claim 117, said system comprising:
three or more sensors and three or more optical elements, said channels disposed about a circumference of the surface so that each of the sensors sense radiation scattered from the surface in directions different from those of radiation sensed by the other sensor(s).

119. The system of claim 109, said device comprising an acousto-optic deflector.

120. The system of claim 109, further comprising a confocal optical detection channel.

121. The system of claim 109, further comprising a polarization element that causes the beam to be polarized.

122. The system of claim 121, further comprising a variable polarization filter in at least one of the channels.

123. The system of claim 109, further comprising a spatial filter.

124. The system of claim 123, wherein said spatial filter is programmable.

125. The system of claim 109, said system further comprising:
two or more sensors and two or more optical elements, each element collecting radiation scattered from the illuminated spot on the surface along a channel and directing the collected and scattered radiation to one of the sensors, causing each of the sensors to provide output signals in response thereto, each of the sensors sensing radiation scattered from the surface in directions away from a specular reflection direction and different from those of radiation sensed by the other sensor(s);
a storage component storing data corresponding to output signals provided by at least two of said sensors in response to scattered radiation from the spot scanned across the surface; and
a processor comparing data corresponding to output signals provided by one of the at least two sensors in response to scattered radiation from the spot scanned across the surface to data corresponding to output signals provided by another one of the at least two sensors in response to scattered radiation from the spot scanned across the surface.

126. The system of claim 125, wherein said processor compares the data to identify and/or classify anomalies.

127. The system of claim 109, said confocal sensor comprising a bright field detector detecting a specular reflection of the radiation in the beam from the illuminated spot on the surface to provide an output signal.

128. The of claim 127, said system further comprising:
two or more sensors; and
a processor processing output signals provided by said sensors, wherein said processor derives one or more threshold level values for processing the output signals provided by said sensors from an output of the bright field detector.

129. The system of claim 128, wherein said one or more threshold level values comprises at least one variable threshold level value.

130. The system of claim 127, said bright field detector comprising a detection element and an optical element that focuses radiation from the illuminated spot to the detection element.

131. The system of claim 109, said system comprising an autoposition detection channel.

132. The system of claim 109, said device causing the beam to scan a serpentine path on the surface.

133. The system of claim 109, said device causing the beam to scan a path on the surface, said system further comprising a registration detection channel that provides a signal for aligning the path with streets on the surface.

134. The system of claim 109, wherein said relative motion between the beam and the surface causes the beam to scan a scan path covering at least a portion of the surface, said path comprising a plurality of scan path segments, wherein each of at least some of such scan path segments has a span shorter than the dimensions of the surface.

135. The system of claim 134, wherein some of said scan path segments form an array.

136. The system of claim 109, wherein said beam of radiation is incident onto the sample surface at an oblique angle.

137. The system of claim 109, wherein said beam of radiation is incident onto the sample surface at a grazing angle.

138. The system of claim 109, wherein said relative motion causes the illuminated spot to scan along adjacent scan path segments on the surface, wherein the adjacent scan path segments overlap.

139. The system of claim 109, said system further comprising:
two or more sensors and two or more optical elements, each element collecting radiation scattered from the illuminated spot on the surface along a channel and directing the collected and scattered radiation to one of the sensors, causing each of the sensors to provide output signals in response thereto, each of the sensors sensing radiation scattered from the surface in directions away from a specular reflection direction and different from those of radiation sensed by the other sensor(s), wherein said sensors are positioned symmetrically in the azimuth.

140. The system of claim 109, said system comprising an imaging detection channel detecting radiation scattered from the illuminated spot on the surface, said imaging channel comprising a photomultiplier tube or a two dimensional detector array performing time delayed integration.

141. An optical scanning method for detection of anomalies on a surface comprising:
directing a focused beam of radiation onto a sample surface to produce an illuminated spot thereon;
causing relative motion between the beam and the surface so that the beam is caused to illuminate different parts of the surface;
detecting radiation from the illuminated spot on the surface by means of a confocal sensor; and
causing a detector to perform time delayed integration in response to radiation from the illuminated spot on the surface in synchronism with the relative motion to provide output signals.

142. The method of claim 141, wherein said causing causes each of at least some of detectors in a two dimensional array of detectors to provide output signals in response to the collected scattered light from each of portions in an array of surface portions in the illuminated spot defining a line of pixels.

143. The system of claim 142, said relative motion causing the beam to scan a first line of pixels in a first scan and a second line of pixels in a subsequent second scan, wherein said causing comprises focusing radiation from at least some of the pixels in the line of pixels to a first line of detectors during the first scan and to a second line of detectors during the second scan, said method further comprising transferring output signals from the first line of detectors to the second line of detectors to perform time delayed integration.

144. The system of claim 141, wherein directing directs the beam to illuminate an elongated spot on the surface.

145. The method of claim 141, further comprising polarizing the beam.

146. The method of claim 145, wherein said polarizing polarizes the beam so that it has S, P or circular polarization.

147. The method of claim 146, wherein said collecting collects radiation of all polarization.

148. The method of claim 145, wherein said polarizing polarizes the beam so that it has S polarization and said collecting collects radiation of S polarization.

149. The method of claim 145, wherein said polarizing polarizes the beam so that it has P polarization and said collecting collects radiation of P polarization.

150. The method of claim 145, wherein said polarizing polarizes the beam so that it has S or P polarization and said collecting collects radiation of all polarization.

151. The method of claim 141, further comprising:
collecting radiation scattered from the illuminated spot on the surface along channels away from a specular reflection direction of the beam and directing the collected and scattered radiation to two or more sensors, causing each of the sensors to provide output signals in response thereto;
storing data corresponding to output signals provided by at least two of the said sensors in response to scattered radiation from the spot scanned across the surface; and
comparing data corresponding to output signals provided by one of the at least two of the said sensor in response to scattered radiation from the spot scanned across the surface to data corresponding to output signals provided by another one of the at least two of the said sensor in response to scattered radiation from the spot scanned across the surface.

152. The method of claim 151, wherein said comparing compares the data to identify and/or classify anomalies.

153. The of claim 141, said method further comprising:
collecting radiation scattered from the illuminated spot on the surface along channels away from a specular reflection direction of the beam and directing the collected and scattered radiation to two or more darkfieldsensors, causing each of the sensors to provide output signals in response thereto.

154. The method of claim 153, wherein the detecting detects a specular reflection of the radiation in the beam from the illuminated spot on the surface by means of a bright field sensor to provide an output signal; said method further comprising processing the output signals of the darkfield sensors, wherein said processing derives one or more threshold level values for processing the output signals provided by said darkfield sensors from an output of the bright field sensor.

155. The system of claim 154, wherein said one or more threshold level values comprises at least one variable threshold level value.

156. The method of claim 154, wherein said relative motion causes the beam to scan a serpentine path on the surface.

157. The method of claim 141, wherein said relative motion causing causes the beam to scan a path on the surface, said method further comprising aligning the path with streets on the surface.

158. The method of claim 141, said relative motion between the beam and the surface causes the beam to scan a scan path covering at least a portion of the surface, said path comprising a plurality of scan path segments, wherein each of at least some of such scan path segments has a span shorter than the dimensions of the surface.

159. The method of claim 158, wherein some of said scan path segments form an array.

160. The method of claim 141, wherein said beam of radiation is incident onto the sample surface at an oblique angle.

161. The method of claim 141, wherein said beam of radiation is incident onto the sample surface at a grazing angle.

162. The method of claim 141, wherein said relative motion causes the illuminated spot to scan along adjacent scan path segments on the surface, wherein the adjacent scan path segments overlap.

163. The method of claim 141, method further comprising:

collecting radiation scattered from the illuminated spot on the surface along channels away from a specular reflection direction of the beam and directing the collected and scattered radiation to three or more sensors, causing each of the sensors to provide output signals in response thereto;

said channels disposed about a circumference of the surface so that each of the sensors sense radiation scattered from the surface in directions different from those of radiation sensed by the other sensor(s).

* * * * *